(12) United States Patent
Djupesland et al.

(10) Patent No.: US 11,730,904 B2
(45) Date of Patent: Aug. 22, 2023

(54) INTRANASAL ADMINISTRATION

(71) Applicant: OptiNose AS, Oslo (NO)

(72) Inventors: Per Gisle Djupesland, Oslo (NO);
Ramy A. Mahmoud, Yardley, PA (US);
Ole A Andreassen, Oslo (NO); Lars T. Westlye, Oslo (NO); Daniel S. Quintana, Oslo (NO); Knut T. Smerud, Oslo (NO); Colin David Sheldrake, Wiltshire (GB)

(73) Assignee: OptiNose, Inc., Yardley, PA (US)

( * ) Notice: Subject to any disclaimer, the term of this patent is extended or adjusted under 35 U.S.C. 154(b) by 243 days.

(21) Appl. No.: 17/338,962

(22) Filed: Jun. 4, 2021

(65) Prior Publication Data
US 2021/0322690 A1 Oct. 21, 2021

Related U.S. Application Data

(63) Continuation of application No. 14/946,389, filed on Nov. 19, 2015, now Pat. No. 11,052,204.
(Continued)

(51) Int. Cl.
*A61M 15/08* (2006.01)
*A61M 15/00* (2006.01)
(Continued)

(52) U.S. Cl.
CPC .......... *A61M 15/08* (2013.01); *A61K 9/0043* (2013.01); *A61K 38/08* (2013.01); *A61K 38/095* (2019.01);
(Continued)

(58) Field of Classification Search
CPC .............. A61M 15/08; A61M 15/0013; A61M 15/0021; A61M 15/0098; A61K 38/095; A61K 9/0043
(Continued)

(56) References Cited

U.S. PATENT DOCUMENTS 605,436 A 6/1898 Kellogg
642,748 A 2/1900 Manners
(Continued)

FOREIGN PATENT DOCUMENTS

CN 1146729 A 4/1997
CN 1280512 A 1/2001
(Continued)

OTHER PUBLICATIONS

Epperson et al., *Intranasal Oxytocin in Obsessive-Compulsive Disorder*, Biol Psychiatry, 40:547-49 (1996).
(Continued)

*Primary Examiner* — Phillip A Gray
(74) *Attorney, Agent, or Firm* — Finnegan, Henderson, Farabow, Garrett & Dunner, LLP

(57) ABSTRACT

A delivery device for and method of modulating a condition relating to social cognition and/or behaviour in a human subject using oxytocin, non-peptide agonists thereof and/or antagonists thereof, comprising: providing a nosepiece to a first nasal cavity of the subject; and providing a supply unit for administering less than 24 IU of oxytocin, non-peptide agonists thereof and/or antagonists thereof through the nosepiece to an upper region posterior of the nasal valve which is innervated by the trigeminal nerve.

23 Claims, 22 Drawing Sheets

Related U.S. Application Data

(60) Provisional application No. 62/081,742, filed on Nov. 19, 2014.

(51) Int. Cl.
| | |
|---|---|
| *A61K 38/22* | (2006.01) |
| *A61K 38/28* | (2006.01) |
| *A61K 38/095* | (2019.01) |
| *A61K 38/08* | (2019.01) |
| *A61K 9/00* | (2006.01) |
| *A61M 29/00* | (2006.01) |
| *A61M 11/00* | (2006.01) |
| *A61M 31/00* | (2006.01) |

(52) U.S. Cl.
CPC .............. *A61K 38/22* (2013.01); *A61K 38/28* (2013.01); *A61M 11/00* (2013.01); *A61M 15/009* (2013.01); *A61M 15/0013* (2014.02); *A61M 15/0021* (2014.02); *A61M 15/0098* (2014.02); *A61M 29/00* (2013.01); *A61M 31/00* (2013.01); *A61M 2202/04* (2013.01); *A61M 2202/064* (2013.01); *A61M 2210/0618* (2013.01)

(58) Field of Classification Search
USPC .......................................................... 604/26
See application file for complete search history.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 5,797,392 A | 8/1998 | Keldmann et al. |
| 5,901,703 A | 5/1999 | Ohki et al. |
| 6,234,365 B1 | 5/2001 | Bougamont et al. |
| 6,648,848 B1 | 11/2003 | Keldmann et al. |
| 6,715,485 B1 | 4/2004 | Djupesland |
| D530,815 S | 10/2006 | Murphy et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,198,240 B2 | 6/2012 | Yeomans et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| D809,128 S | 1/2018 | Djupesland |
| 9,949,923 B2 | 4/2018 | Djupesland |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2004/0235956 A1 | 11/2004 | Quay |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0054843 A1 | 3/2007 | Yeomans et al. |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0181880 A1 | 7/2009 | Yeomans et al. |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0147292 A1 | 6/2010 | Hamaguchi et al. |
| 2010/0199984 A1 | 8/2010 | Williams et al. |
| 2010/0242959 A1 | 9/2010 | Djupesland et al. |
| 2010/0282246 A1* | 11/2010 | Djupesland ....... A61M 15/0098 128/200.14 |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0120456 A1 | 5/2011 | Immel |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |

(56) References Cited

U.S. PATENT DOCUMENTS

| | | |
|---|---|---|
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| CN | 101056666 A | 10/2007 |
| CN | 101723143 A | 6/2010 |
| CN | 101801446 A | 8/2010 |
| CN | 101918061 A | 12/2010 |
| CN | 103237570 A | 8/2013 |
| GB | 2 400 565 A | 10/2004 |
| GB | 2 437 488 A | 10/2007 |
| GB | 2 438 834 A | 12/2007 |
| JP | 09-135901 A | 5/1997 |
| JP | 2007-528248 A | 10/2007 |
| JP | 2008-62974 A | 3/2008 |
| JP | 2011-511674 A | 4/2011 |
| RU | 2 383 358 C2 | 11/2009 |
| RU | 112 044 U1 | 1/2012 |
| WO | WO 96/22802 | 8/1996 |
| WO | WO 98/53869 | 12/1998 |
| WO | WO 99/13930 | 3/1999 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2005/087615 A1 | 9/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/042452 A1 | 4/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/012137 A1 | 1/2009 |
| WO | WO 2009/044172 | 4/2009 |
| WO | WO 2009/100383 A2 | 8/2009 |
| WO | WO 2010/029441 | 3/2010 |
| WO | WO 2012/035427 | 3/2012 |
| WO | WO 2012/076479 A1 | 6/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |
| WO | WO 2020/070321 | 4/2020 |

OTHER PUBLICATIONS

Kovács et al., *Oxytocin and Addiction: A Review*, Psychoneuroendocrinology, 23(8):945-62 (1998).

Ross et al., *Oxytocin and the neural mechanisms regulating social cognition and affiliative behavior*, Front Neuroendocrinol, 30(4):534-547 (Oct. 2009).

ClinicalTrials.gov archive, NCT01028677, *Oxytocin Treatment of Schizophrenia* (Dec. 8, 2009).

ClinicalTrials.gov archive, NCT01983514, *Effects of Intranasal Administration of a Single Dose of Oxytocin Using a Novel Device in Healthy Adults* (Apr. 23, 2014).

Guastella et al., *Intranasal oxytocin improves emotion recognition for youth with autism spectrum disorders*, 67(7):692-694 (2010).

Oxytocin IU, *Oxytocin Leaflet* (Sep. 2012).

Cindy H. Dubin, *Nothing to Sneeze At*, Pharmaceutical Formulation & Quality Magazine (Jan. 29, 2003).

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset Via A Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

(56) References Cited

OTHER PUBLICATIONS

Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using A Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment Of Mild-to-Moderate Nasal Polyposis with Fluticasone Delivered By A Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered By a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *A VP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

* cited by examiner

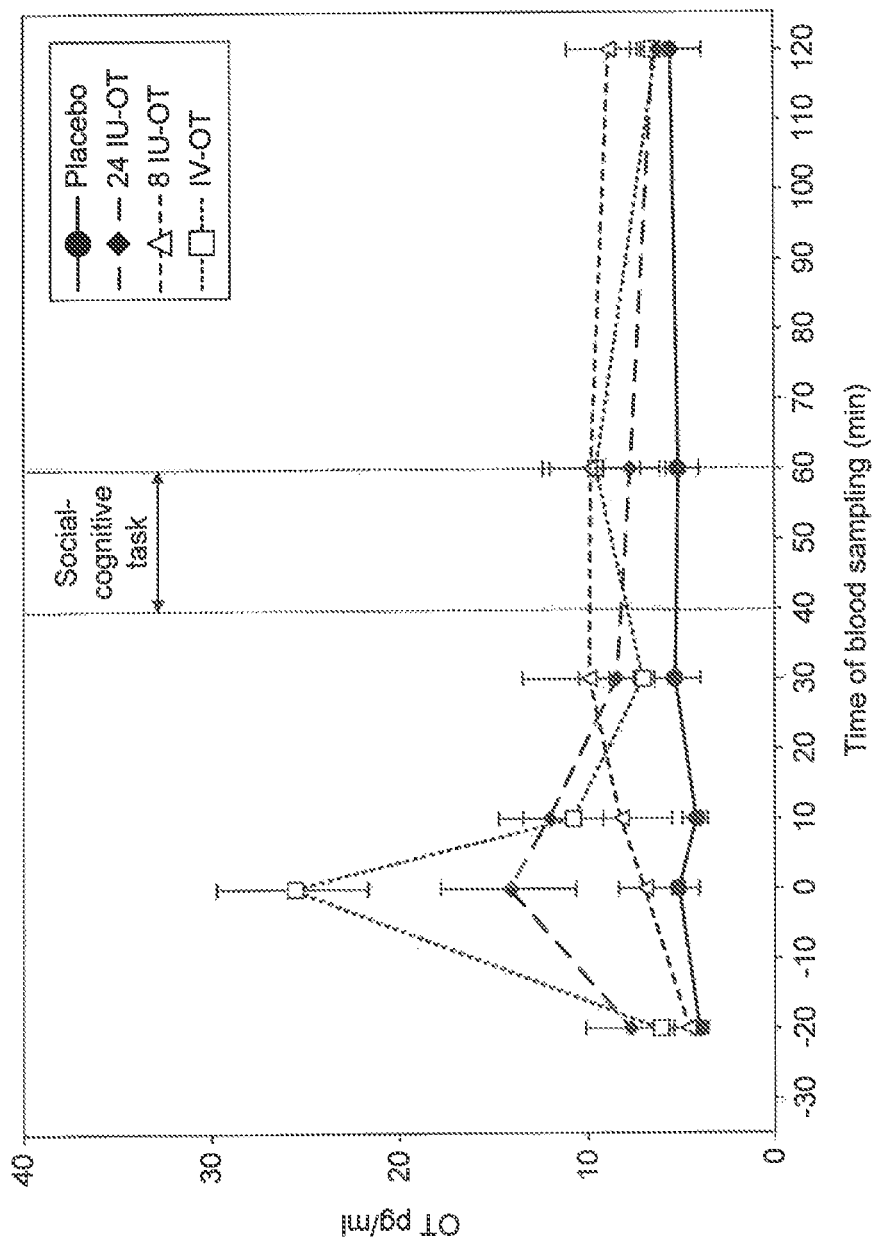

INTRANASAL ADMINISTRATION

This application is a continuation application of U.S. application Ser. No. 14/946,389, filed on Nov. 19, 2015, which claims priority to U.S. Provisional Application No. 62/081,742, filed on Nov. 19, 2014. The disclosure of each of the above applications is incorporated herein by reference in its entirety.

FIELD OF THE INVENTION

The present invention relates to the intranasal administration of oxytocin (OT), especially for the modulation of social cognition and/or behavior, being mental and/or behavioral operations underlying social interactions, and also to the intranasal administration of other peptides, including Orexin-A, especially for the treatment of narcolepsy, and insulin, especially for the treatment of diabetes.

BACKGROUND OF THE INVENTION

A growing body of evidence demonstrates a role of OT in social cognition and behavior[1-3]. For instance, a single administration of OT has increased empathy[4-5], trust[6], group-serving behaviours[7-8], sensitivity of eye gaze[9], and theory-of-mind performance in healthy individuals[10] and in patients with psychiatric disorders[11]. OT has also been proposed as a novel therapy for disorders characterized by social dysfunction, such as autism and schizophrenia spectrum disorders[12-13].

Despite initial promise, however, recent work has either failed to identify changes in social behavior after OT administration[14] or has provided results that are only significant for specific subgroups or contexts[15]. These mixed results have been largely attributed to such contextual and individual differences[16], and factors that may influence biological activity of exogenous OT have yet to be thoroughly investigated[15-18].

The present inventors postulate that other factors to dose and delivery method may influence biological activity of exogenous OT, and similarly to other peptides, including Orexin-A and insulin.

Olfactory nerve fibres innervate a limited segment of the deep upper narrow nasal passage, while the trigeminal nerve provides sensory and parasympathetic innervation to the deep upper and posterior segments of the nose. Drug transport along these cranial nerve fibres may offer a potential direct route to the central nervous system (CNS)[15,23] circumventing the blood-brain barrier (BBB), and this segment is not adequately targeted by conventional nasal spray devices[15,26].

The present inventors postulate that, by virtue of nose-to-brain activity, the targeted intranasal administration of OT to this innervated segment of the nasal passage could enable pharmacodynamic effects in the brain disproportionate to what would be achieved by absorption into the blood, and that this method of targeted delivery may improve the reliability, therapeutic index, and effect magnitude of OT treatment effects due to improved drug deposition[15,31-32].

An unchallenged assumption in the literature that would benefit from closer experimental scrutiny in humans is that intranasal administration is the best means of delivering OT to modulate social cognition and behaviour[15].

Despite early work demonstrating that intravenous (IV) administration can influence social behavior and cognition[33-34]—presumably via blood absorption and subsequent action across the BBB—subsequent human studies assessing the effect of OT on cognitive functions have used methods that deliver OT via the nasal cavity. Although there is a strong theoretical basis that intranasal delivery is a more appropriate means of administering OT, a controlled comparison of pharmacodynamics (PD) effects after intranasal (i.e., nose-to-brain) and intravenous (i.e., transportation across the BBB) administration has not been done.

Furthermore, in relation to the dosing regimen, the majority of intranasal OT studies have evaluated between 20 and 40 international units (IU)[36]. There is no comprehensive empirical evidence substantiating this dosage[37-38], though successful in other disciplines (e.g. obstetrics)[39]. This is despite the negative long-term effects of OT treatment observed in non-human adolescent mammals[40], and the presence of OT and cross-reactive vasopressin (AVP) receptors throughout the body[41] that are involved in a variety of homeostatic functions related to observed side effects[42].

It is an aim of the present invention to provide for improved efficacy in the intranasal administration of oxytocin (OT), especially for the modulation of social cognition and/or behavior, and other peptides, including Orexin-A, especially for the treatment of narcolepsy, and insulin, especially for the treatment of diabetes.

SUMMARY OF THE INVENTION

In one aspect the present invention provides a method of modulating conditions relating to social cognition and/or behaviour in a human subject using oxytocin, non-peptide agonists thereof and/or antagonists thereof, comprising: providing a nosepiece to a first nasal cavity of the subject; and administering less than 24 IU of oxytocin, non-peptide agonists thereof and/or antagonists thereof to an upper region posterior of the nasal valve which is innervated by the trigeminal nerve.

In another aspect the present invention provides a method of modulating a condition in a human subject using a peptide, non-peptide agonists thereof and/or antagonists thereof, comprising: providing a nosepiece to a first nasal cavity of the subject; and administering less than 24 IU of a peptide, non-peptide agonists thereof and/or antagonists thereof through the nosepiece to an upper region posterior of the nasal valve which is innervated by the trigeminal nerve.

In a further aspect the present invention provides a nosepiece for delivering substance to a nasal cavity of a subject, the nosepiece comprising: a first, inner body part; and a second, outer body part which is disposed about at least a distal portion of the inner body part and defines a tip; wherein the inner body part comprises a base portion which defines a flow passage therethrough, and a projection at the distal end thereof which supports the tip and confers a rigidity in the sagittal direction, which enables the tip to open fleshy tissue at an upper region of the nasal valve and thereby expand an open area of the nasal valve, and a flexibility in a lateral direction, orthogonal to the sagittal plane, which facilitates insertion of the tip into the nasal valve.

In a yet further aspect the present invention provides a nosepiece for delivering substance to a nasal cavity of a subject, the nosepiece comprising a body part which comprises a base portion which defines a flow passage therethrough, and a projection at a distal end of the base portion which at least in part provides a tip of the nosepiece and confers a rigidity in the sagittal direction, which enables the tip to open fleshy tissue at an upper region of the nasal valve and thereby expand an open area of the nasal valve, and a flexibility in a lateral direction, orthogonal to the sagittal plane, which facilitates insertion of the tip into the nasal valve.

DESCRIPTION OF THE FIGURES

Preferred embodiments of the present invention will now be described hereinbelow by way of example only with reference to the accompanying drawings, in which:

FIG. 7(a) represents the mean OT plasma concentration over time after the administrations of 8 IU-OT, 24 IU-OT, IV-OT and Placebo, with error bars representing standard error of the mean;

DETAILED DESCRIPTION OF THE EMBODIMENTS

Device

Figure 1A:
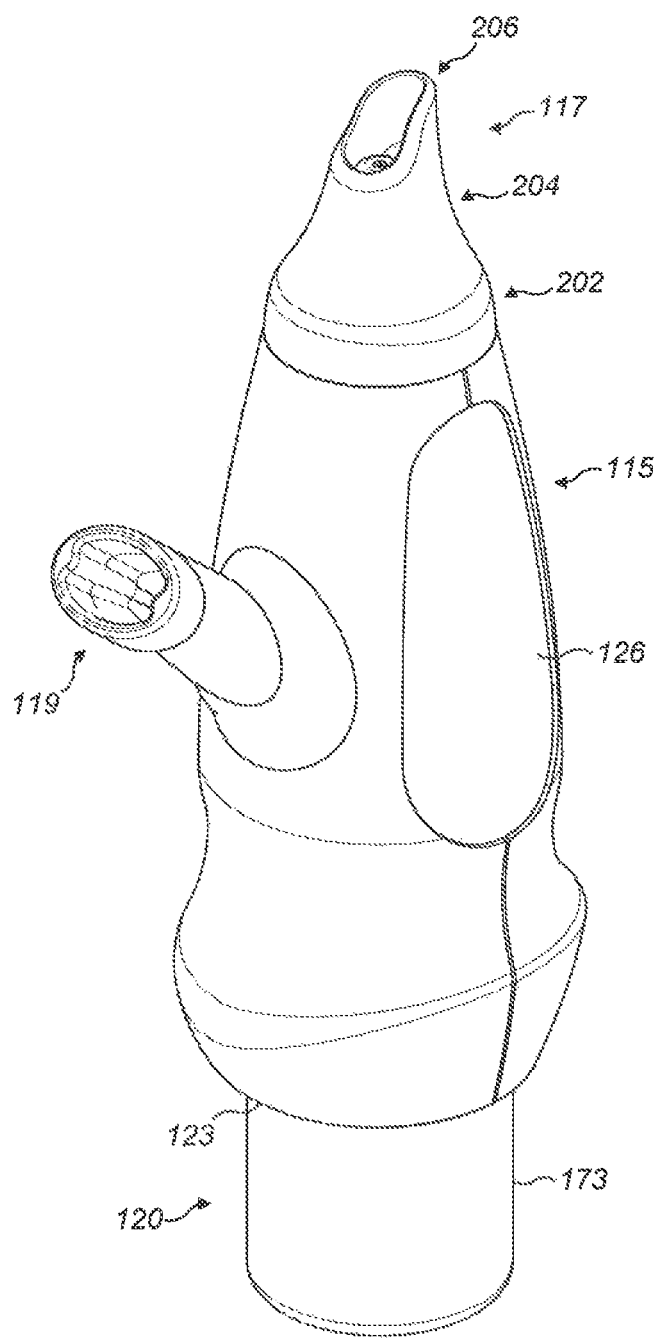
FIGS. 1(a) to (c) illustrate a delivery device in accordance with one embodiment of the present invention.
Figure 1B:
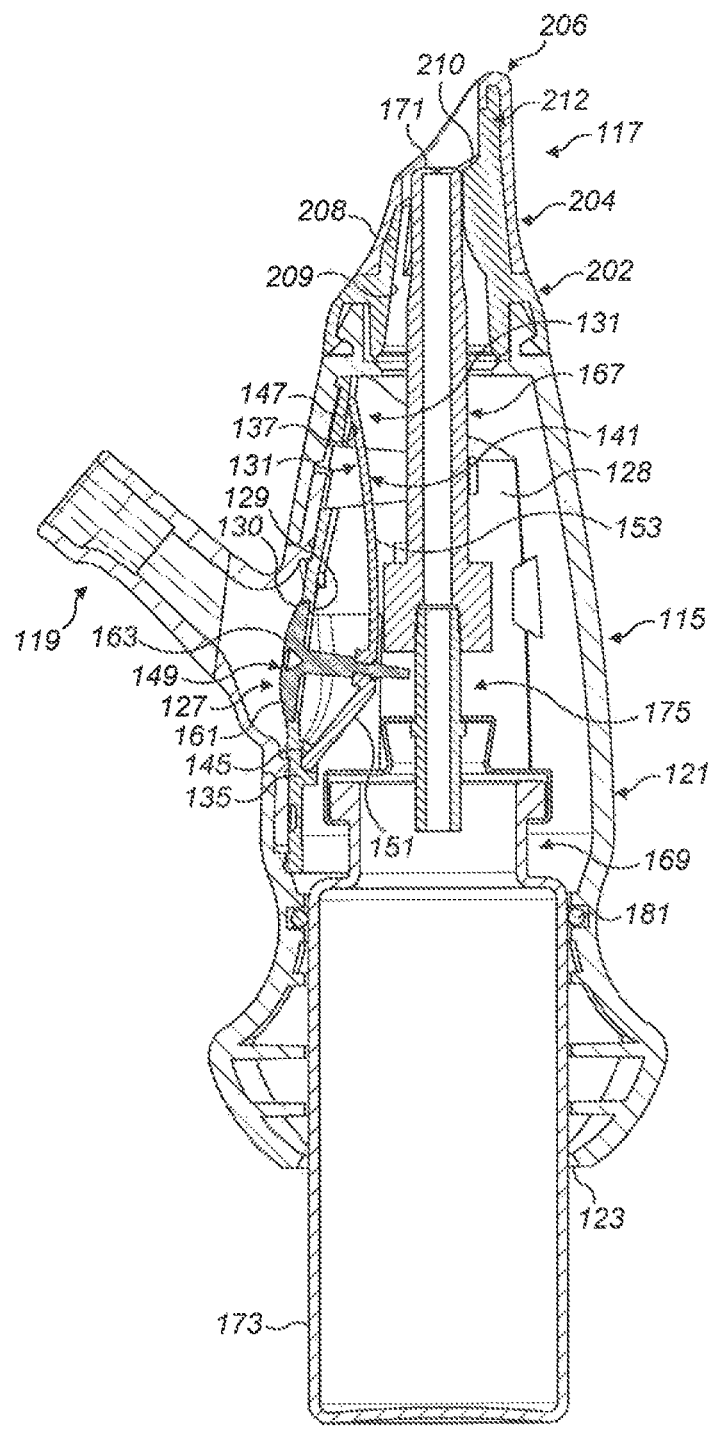
Figure 1C:
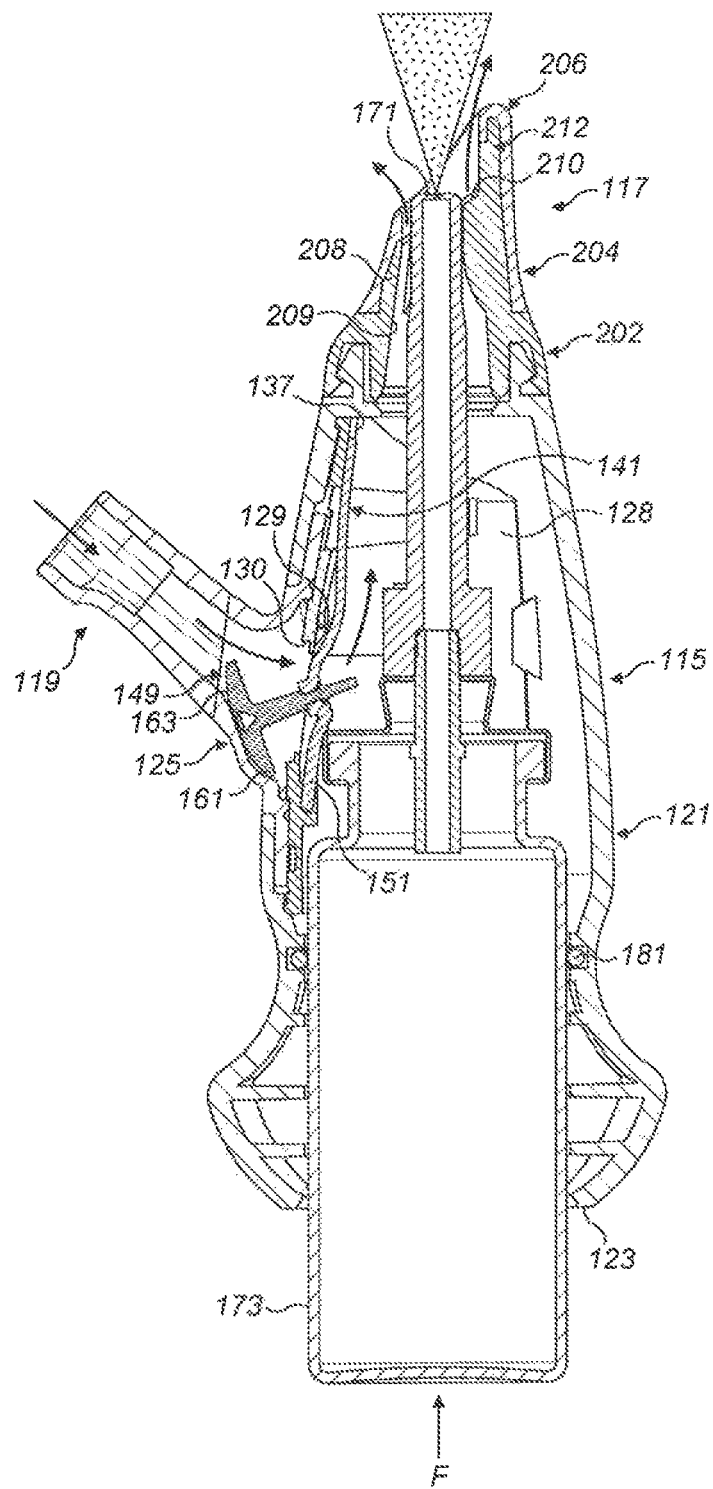

FIGS. 1(a) to (c) illustrate a manually-actuated nasal delivery device in accordance with one embodiment of the present invention.

The delivery device comprises a housing 115, a nosepiece 117 for fitting in a nasal cavity of a subject, a mouthpiece 119 into which the subject in use exhales, such as to enable delivery of an air flow into and through the nasal airway of the subject on exhalation by the subject through the mouthpiece 119, and a delivery unit 120, which is manually actuatable to deliver substance to the nasal cavity of the subject.

The housing 115 comprises a body member 121, in this embodiment of substantially elongate, tubular section which includes an aperture 123 at one end thereof, through which projects an actuating part of the delivery unit 120, in this embodiment as defined by the base of a substance-containing chamber 173 of a substance-supply unit 169.

Figure 4:
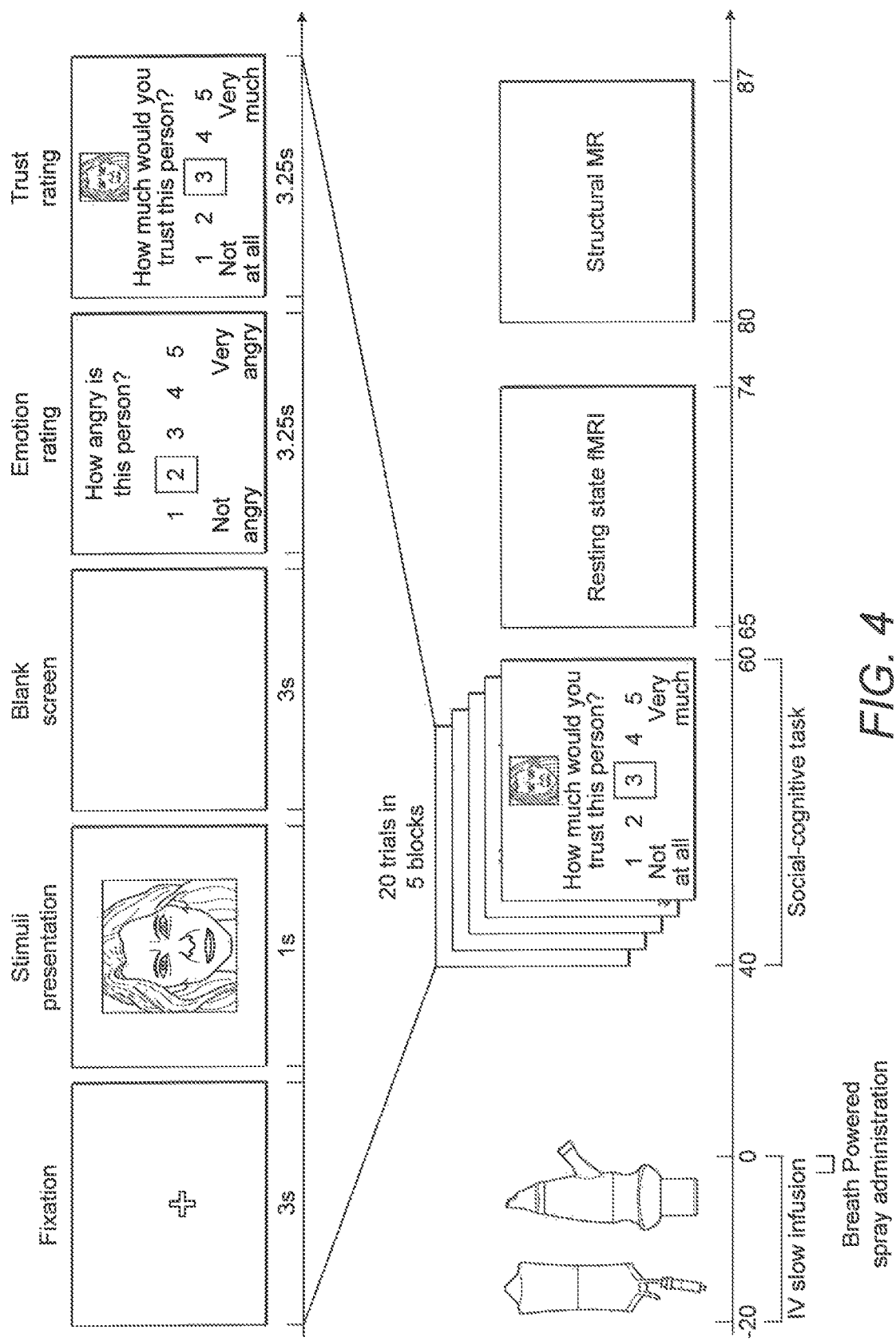
FIG. 4 illustrates the social-cognitive task design of the study.

The housing 115 further comprises a valve assembly 127 which is fluidly connected to the nosepiece 117 and the mouthpiece 119, and operable between closed and open configurations, as illustrated in FIGS. 3 and 4, such as to provide for an air flow, in this embodiment in the form of a burst of air, through the nosepiece 117 simultaneously with actuation of the delivery unit 120, as will be described in more detail hereinbelow.

The valve assembly 127 comprises a main, body element 128 which includes a valve seat 129 defining a valve opening 130, and a valve element 131 which is movably disposed to the body element 128 between closed and open positions, as illustrated in FIGS. 1(b) and (c).

As particularly illustrated in FIG. 1(c), the body element 128 comprises a pivot 135, in this embodiment to one, lower side of the valve seat 129, to which one end 145 of the valve element 131 is pivoted, and a sliding surface 137, in this embodiment to the other, upper side of the valve seat 129, against which the other end 147 of the valve element 131 is slideable.

The valve element 131 comprises an elongate arm 141, in this embodiment a flexible arm, one end 145, in this embodiment the lower end, of which is pivoted to the pivot 135 of the body element 128, and the other, upper end 147 of which slideably engages the sliding surface 137 of the body element 128, and a valve member 149 which is supported by the arm 141.

In this embodiment the arm 141 comprises a first, here lower, arm section 151, which is biased, here inwardly, such that, when the valve element 131 is in the closed, rest position, the lower arm section 151 is inclined inwardly relative to the longitudinal axis of the housing 115 and engageable by the substance-supply unit 169 when manually actuated to move the valve element 131 to the open position, as will be described in more detail hereinbelow.

In this embodiment the arm 141 further comprises a second, here upper, arm section 153, which engages the sliding surface 137 of the body element 128 and acts to bias the valve element 131 to the closed position.

In this embodiment the valve member 149 comprises a seal 161, in this embodiment a flexible or resilient element, which acts to close the valve opening 130 as defined by the valve seat 129 when the valve element 131 is in the closed position, and a support 163 which supports a central region of the seal 161.

With this configuration, where the seal 161 is centrally supported, when the valve element 131 is moved to the open position, the support 163 biases the central region of the seal 161, causing the seal 161 to bulge outwardly in this central region and thus provide that the seal 161 engages the valve seat 129 only at the peripheral edge of the seal 161, until the point is reached when the seal 161 is suddenly and explosively released from the valve seat 129.

This mode of release is believed to be particularly effective in the present application where it is desired to achieve a sudden, initial burst of air flow, in that substantially the entire sealing surface of the seal 161 is released in one instant, which compares to an alternative mode of a peeling-type release, where a smaller section of a sealing surface is released, followed by the remainder of the sealing surface, which tends to provide a smaller initial burst pressure.

In this embodiment the delivery unit 120 comprises an outlet unit 167 for delivering substance into the nasal airway of the subject, and a substance-supply unit 169 for delivering substance to the outlet unit 167.

In this embodiment the outlet unit 167 comprises a nozzle 171 for delivering substance to the nasal airway of the subject. In this embodiment the nozzle 171 is configured to provide an aerosol spray. In an alternative embodiment, for the delivery of a liquid, the nozzle 171 could be configured to deliver a liquid jet as a column of liquid.

In a preferred embodiment the distal end of the outlet unit 167 is configured to extend at least about 2 cm, preferably at least about 3 cm, and more preferably from about 2 cm to about 3 cm, into the nasal cavity of the subject.

In this embodiment the substance supply unit 169 is a pump unit, which comprises a substance-containing chamber 173 which contains substance and extends from the aperture 123 in the housing 115 as the actuating part of the substance-supply unit 169, and a mechanical delivery pump 175 which is actuatable, here by depression of the substance-containing chamber 173, typically by a finger or thumb of the subject, to deliver a metered dose of substance from the substance-containing chamber 173 to the outlet unit 167 and from the nozzle 171 thereof, here as an aerosol spray.

In this embodiment the substance-containing chamber 173, when depressed to actuate the substance supply unit 169, engages the lower arm section 151 of the arm 141 of the valve element 131, such as simultaneously to provide for actuation of the substance-supply unit 169 and opening of the seal 161 of the valve element 131, whereby substance, here in the form of a spray, and an air flow, here as a burst of air, are simultaneously delivered to the nasal cavity of the subject.

In this embodiment the mechanical delivery pump 175 is a liquid delivery pump for delivering a metered dose of substance.

In this embodiment the substance-supply unit 169 is a multi-dose unit for delivering a plurality of metered doses of substance in successive delivery operations.

In this embodiment the housing 115 further comprises a sealing member 181, here an annular seal, in the form of an O-ring, which slideably receives the substance-containing chamber 173 of the substance-supply unit 169, such as to prevent the escape of the delivered air flow from the aperture 123 in the housing 115.

FIGS. 2(a) to (e) and 3(a) to (e) illustrate the nosepiece 117 of the described embodiment.

Figure 2A:
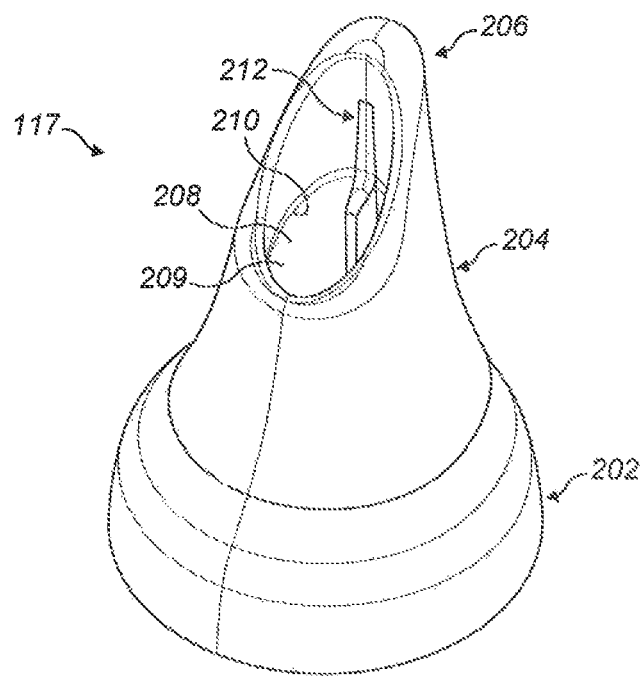
FIGS. 2(a) to (e) illustrate perspective, lateral, front, underneath and longitudinal sectional views (along section A-A) of the nosepiece of the device of FIGS. 1(a) to (c)
Figure 2B:
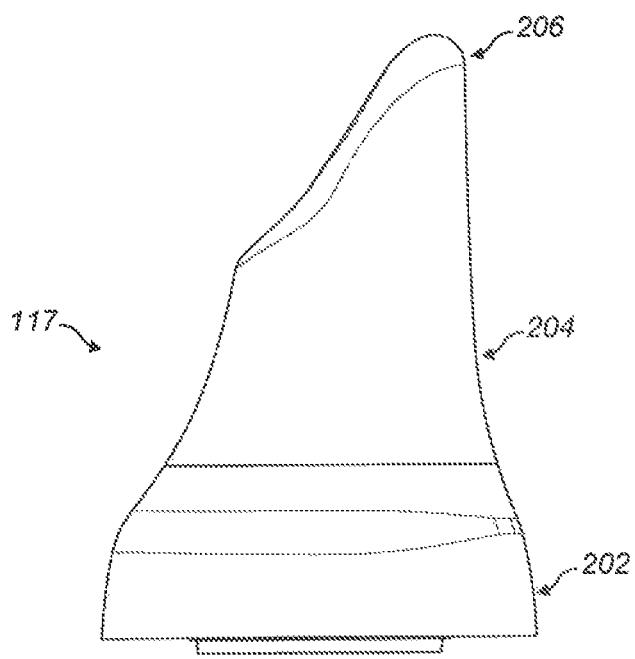
Figure 2C:
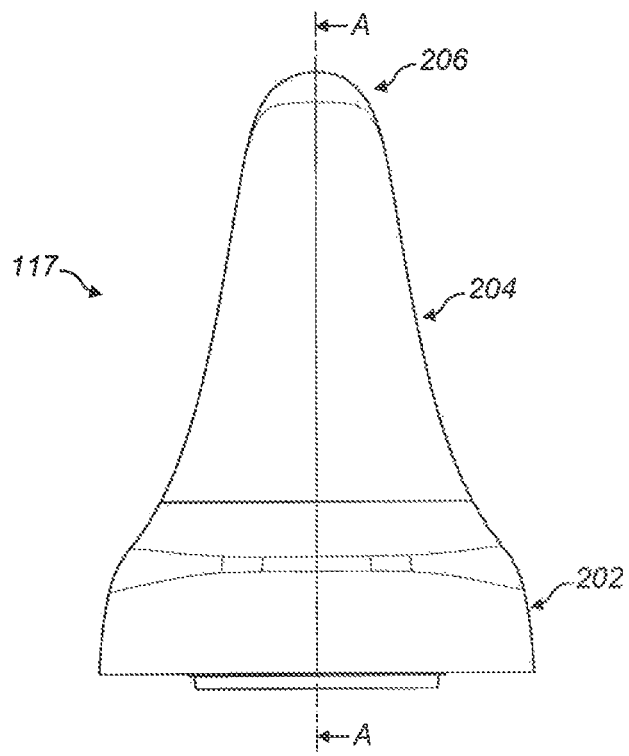
Figure 2D:
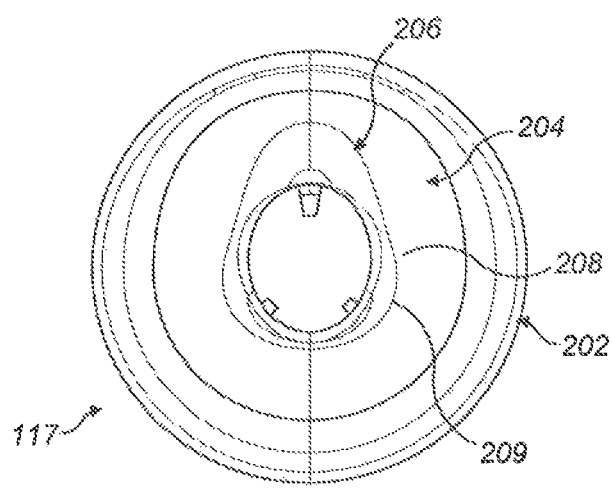
Figure 2E:
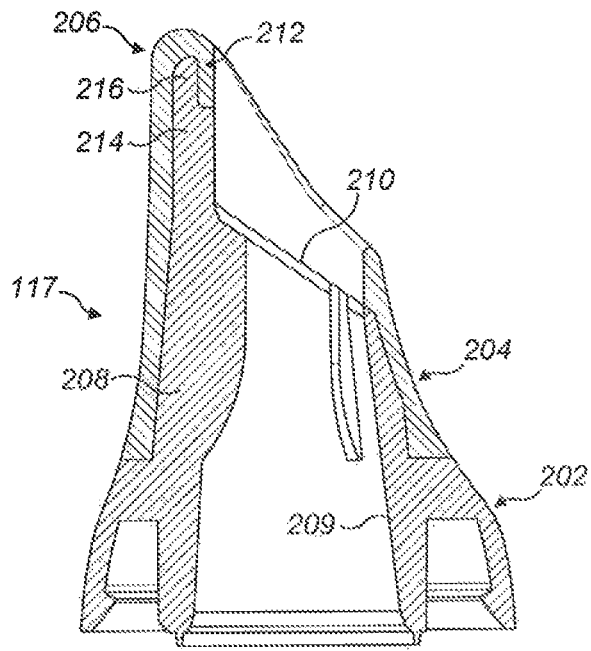
Figure 3A:
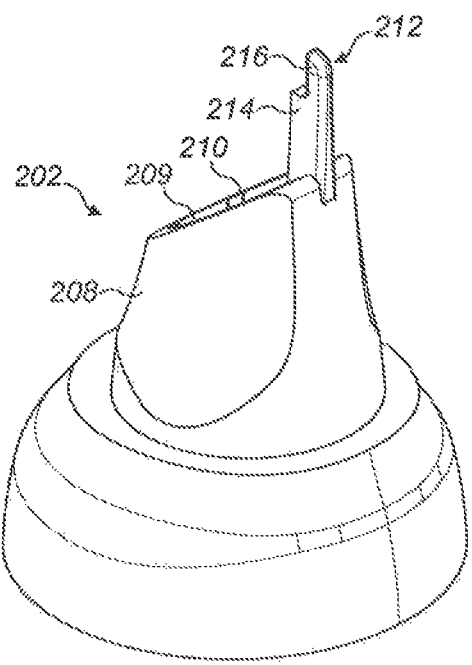
FIGS. 3(a) to (e) illustrate perspective, lateral, front, underneath and longitudinal sectional views (along section B-B) of the inner body part of the nosepiece of the device of FIGS. 1(a) to (c)
Figure 3B:
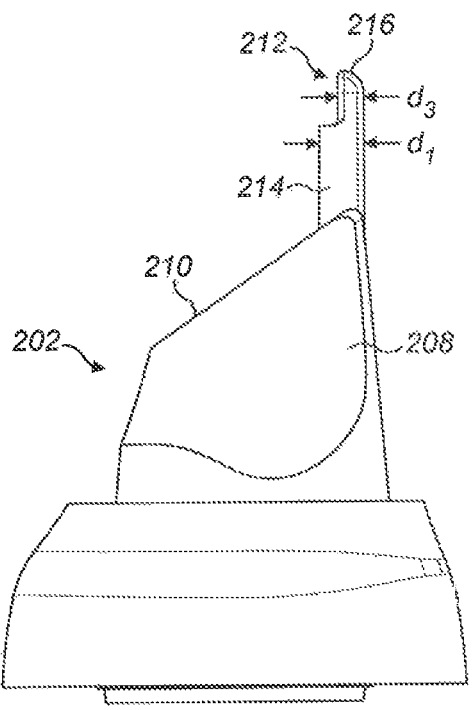
Figure 3C:
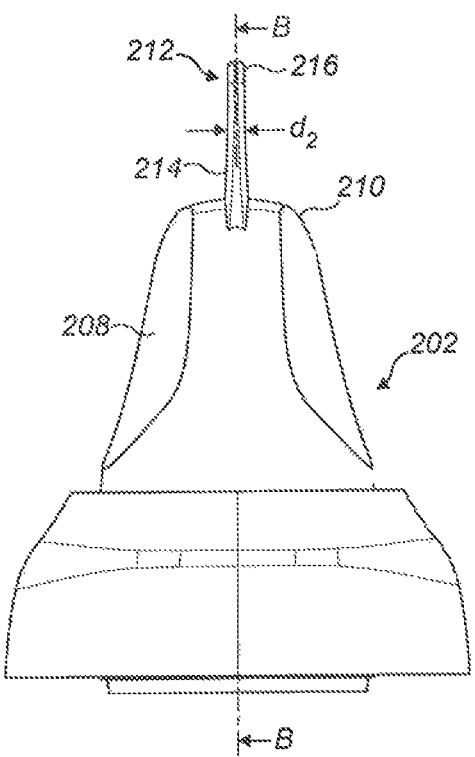
Figure 3D:
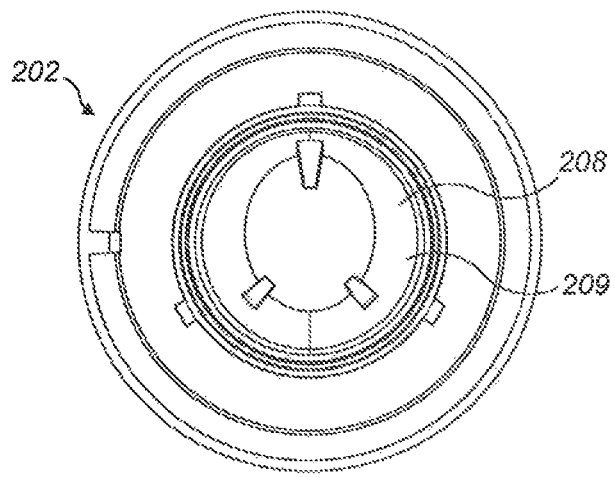
Figure 3E:
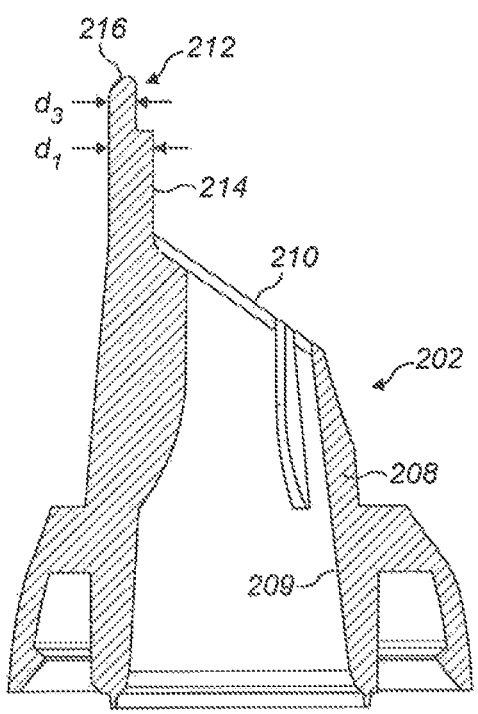

As particularly illustrated in FIG. 2(e), the nosepiece 117 is formed of two body parts 202, 204, a first, inner body part 202, here formed of a plastics material, and a second, outer body part 204, here formed of a softer, resilient material, such as a rubber or elastomeric material, which is disposed about the distal end of the inner body part 202 and defines a tip element 206.

In this embodiment the inner body part 202 is formed of an acrylonitrile butadiene styrene (ABS) plastic, here Guardian/Lustran® ABS 308 (as supplied by Ineos ABS (USA) Corporation).

In this embodiment the outer body part 204 is formed of a thermoplastic elastomer (TPE), here Versaflex® OM 1040X-1 (as supplied by GLS/PolyOne Corporation), having a Shore A hardness of 42.

As particularly illustrated in FIGS. 3(a) to (e), in this embodiment the inner body part 202 comprises a base portion 208 which defines a flow passage 209 therethrough, and a projection 112 at the distal, forwardmost end thereof which supports the tip 106 of the nosepiece 117.

In this embodiment the distal, forwardmost end of the base portion 208 defines a surface 210 which tapers or is inclined in relation to the longitudinal axis of the nosepiece 117, such that the surface 210 of the base portion 208 is inclined in an direction away from the distal end of the projection 212, and the base portion 208 is shorter at that side which is opposite to the projection 212.

The projection 112 is configured to confer a rigidity in the sagittal direction, which enables the tip 206 of the nosepiece 117 to open the fleshy tissue at upper region of the nasal valve and thereby expand the open area of the nasal valve, and a flexibility in the lateral direction, which facilitates insertion of the tip 206 of the nosepiece 117 into the nasal valve. In this embodiment, from measurement by acoustic rhinometry (AR), the nosepiece 117 provides for expansion of the area of the nasal valve to an area which is at least twice the area of the nasal valve when unexpanded and in a rest state.

In this embodiment the projection 212 extends axially in substantially parallel relation to the longitudinal axis of the nosepiece 117.

In this embodiment the projection 212 has the form of a blade, with a length d1 in the sagittal direction being greater than a length d2 in the lateral direction.

In this embodiment the length d1 in the sagittal direction is 1.5 times greater than the mean length d2 in the lateral direction.

In one embodiment the length d1 in the sagittal direction is 1.7 times greater than the mean length d2 in the lateral direction.

In this embodiment the length d1 in the sagittal direction is 1.9 times greater than the mean length d2 in the lateral direction.

In this embodiment the length d1 in the sagittal direction is 2 times greater than the mean length d2 in the lateral direction.

In this embodiment the projection 212 has a length d1 in the sagittal direction of about 2 mm.

In this embodiment the projection 212 has a length d2 in the lateral direction of about 1 mm.

In this embodiment the projection 212 has a main body section 214 and a tip section 216 which has a shorter length d3 in the sagittal direction than the length d1 of the main body section 214, here defining a step at an inner edge thereof.

In this embodiment the projection 212 has a tapering lateral cross-section along its length, with the length d2 in the lateral direction reducing in cross-section along its length towards the distal end.

In this embodiment the length d2 in the lateral direction reduces from about 1.1 mm to about 0.8 mm from the proximal to the distal end of the projection 212.

Study

A randomized, double-blind, double-dummy, crossover study was performed, in which 18 healthy male adults were randomly assigned, and 16 completed four single-dose treatments; these being (1) the intranasal administration of a liquid spray of 8 IU of OT delivered using the device of FIGS. 1(a) to (c) (hereinafter 8 IU-OT), (2) the intranasal administration of a liquid spray of 24 IU of OT delivered using the device of FIGS. 1(a) to (c) (hereinafter 24 IU-OT), (3) the intravenous delivery of 1 IU of OT (hereinafter IV), and (4) the intranasal administration of a liquid spray of a placebo using the device of FIGS. 1(a) to (c) (hereinafter Placebo).

This study compared pharmacodynamic (PD) effect of OT on social cognition and behavior, as indexed by the presentation of emotional stimuli and in particular amygdala activity.

In order to examine the neural correlates of OT's behavioral and cognitive effects, researchers have adopted brain-imaging tools such as functional magnetic resonance imaging (fMRI). Converging evidence from this field suggests the amygdala, a key brain region for emotion regulation[86], processing[87] and detection[113], is an important target of OT administration. The modulation of amygdala activity in response to emotional stimuli is arguably the most replicated and well-characterized result within brain imaging and intranasal OT studies[88,89,114-117]. Irrespective of this prior work, however, it is not clear how OT travels to the brain or which OT dose is more likely to modulate the recruitment of amygdala during the presentation of emotional stimuli. By comparing amygdala activity after both intranasal and intravenous OT administration, when comparable blood levels are achieved, research can determine if neural modulation occurs via direct nose-to-brain transport (as currently assumed) or through systemically circulating OT crossing the BBB. There is both animal[70] and human[33-34] research to suggest systemic OT can influence social behavior and cognition—however, research has not yet evaluated amygdala activity after intravenous delivery with an intranasal OT comparator.

Recent theories also underscore OT's role in the facilitation of approach-related behaviours[118] and the modulation of social stimuli salience[16]. Given the established relationship between cognitive resource allocation and pupil dilation[119-120], pupilometry offers a non-invasive neurobiological measure of engagement towards emotional stimuli. Research indicates that intranasal OT enhances pupil dilation[55] and the salience of social cues[121]. However, the relationship between amygdala activity and pupil-indexed cognitive engagement has yet to be explored and may contribute to a better understanding of the effects of OT.

Primary outcomes were the evaluation of facial emotional expression, in particular in relation to amygdala activity, and secondary outcomes included pharmacokinetic (PK) profiles and ratings of trustworthiness.

This study hypothesized a main effect of the administration of 8 IU-OT and 24 IU-OT on the perceived intensity of anger, and that this effect would be more pronounced with ambiguous emotional stimuli compared to stimuli with less ambiguous emotional expressions.

This study examined dose-dependent effects of 8 IU-OT and 24 IU-OT.

This study also investigated the impact of OT on trust ratings of the same facial stimuli.

In order to characterize PK and evaluate potentially different relationships between PK and PD by method of drug delivery, the time course of blood plasma concentrations of OT and physiologically interacting substances vasopressin (AVP) and cortisol were measured following treatment. Modulation of social cognition after 8 IU-OT and 24 IU-OT administration, but not after IV-OT producing comparable blood exposure, would provide evidence that 8 IU-OT and 24 IU-OT administration is, at least in part, directly acting on the brain rather than across the BBB.

Eligible participants were males between the ages of 18 to 35, in good physical and mental health. Exclusion criteria included use of any medications within the last 14 days, history of alcohol or drug abuse, clinically relevant history of physical (including renal, cardiac, endocrine, pulmonary, hepatic, nervous, gastrointestinal, hematological and metabolic disorders), or psychiatric illness, and IQ<75. Fifty-seven male volunteers were assessed for eligibility, and 18 participants were selected aged 20-30 years (M=23.81, SD=3.33). Two participants withdrew after enrollment [1 withdrew after the first session, and the other withdrew after completing three sessions], and data from these participants is not included in the analyses.

A screening visit occurred between 3-21 days prior to randomization. The Wechsler Abbreviated Scale of Intelligence[52] and the Mini-International Neuropsychiatric Interview[53] were used to index IQ and confirm the absence of psychiatric illness, respectively. A physical examination was performed, including ECG and the collection of routine blood samples. In addition, an otolaryngologist confirmed normal nasal anatomy and patency in participants (via physical examination) and acoustic rhinometry (AR) data were collected (SRE 2000; Rhinometrics, Lynge, Denmark). Three measures were calculated from the AR data: Minimum cross-sectional area (MCA; i.e., the narrowest section of the nasal cavity), total volume from nostril to 5 cm deep (TV0-5), and total volume from 2-5 cm deep (TV2-5).

A randomized, placebo-controlled, double-blind, double-dummy, four-period crossover design was used for this study. Participants were randomized to one of four treatment sequences, using a four-period four-treatment Latin square method (ACDB-BDCA-CBAD-DABC in a 4:4:4:4 ratio), with a period of at least six days between treatments to prevent potential carry-over effects. Both the participants and research team were blinded to treatment using visually matching devices and IV apparatus during data collection.

In this study, the delivery device capitalizes on two aspects of nasal anatomy to facilitate delivery to the respiratory and nasal epithelia[32]. Firstly, as the user is blowing through the mouth against a resistance, the soft palate automatically closes, isolating the nasal cavity from the oral cavity, preventing lung deposition and limiting gastrointestinal deposition[23].

Secondly, in conjunction with closure of the soft palate, an optimized nosepiece is employed that allows deeper insertion to directs the exhaled breath and OT into the upper-posterior nasal cavity segments[23].

The 8 IU-OT, 24 IU-OT and Placebo formulations were supplied by Sigma-Tau Industrie Farmaceutiche Riunite S.p.A. The Placebo formulation was 0.9% sodium chloride.

The IV-OT formulation was supplied by AS Grindeks, Riga, Latvia was supplied as a 10 IU/ml formulation and added to a 0.9% sodium chloride solution for infusion shortly before administration (600 ml/hour over 20 minutes). The intravenous dosage and infusion rate was chosen so as to generate peripheral OT concentrations that are equivalent to intranasal delivery, as confirmed by experiment.

In order to ensure appropriate use and standardization, participants were trained on the use of the intranasal delivery device by watching a demonstration video, following written instructions, and administering practice saline sprays under the supervision of trained research staff during the screening session.

At the beginning of each experimental session, exclusion and inclusion criteria were confirmed and the State-Trait Anxiety Inventory 54 was administered. Blood samples were taken to assess routine measures and acoustic rhinometry (AR) was performed (per procedures during screening) to confirm that the nasal cavity environment did not significantly differ between sessions due to nasal cycles[24].

Participants completed the social-cognitive task 40 minutes after treatment in a magnetic resonance imaging (MRI) scanner while functional MRI and physiology data was recorded.

Participants were presented with visual stimuli through MRI-compatible goggles (VisualSystem; NordicNeuroLab, Bergen, Norway) using E-Prime 2.0 (Psychology Software Tools, PA, USA), and responded using a grip response collection system (ResponseGrip, NordicNeuroLab, Bergen, Norway).

Participants were presented with 20 male and 20 female faces[55] displaying angry, happy, and emotionally ambiguous facial expressions [derived from the Karolinska Directed Emotional Faces database[56]] and 20 images of geometrical shapes. The social-cognitive task consisted of five blocks of 20 trials, as illustrated in FIG. 4. Each trial of approximately 140 s duration comprised the following sequence: Fixation cross of 3 s duration→Stimulus (face/shapes) presentation of 1 s duration→Q1 of 3.25 s duration (maximum response window)→Q2 of 3.25 s duration (maximum response window).

For the evaluation of the faces, participants were asked a first question (Q1) which was either: How angry is this person? (anchors: not angry-very angry) or, How happy is this person? (anchors: not happy-very happy), and a second question (Q2), which was always the same: How much would you trust this person? (anchors: not at all-very much). For both questions, participants were asked to rank their answer on a visual analogue scale (VAS) from 1 to 5, with location of the cursor on the VAS randomized on the presentation of each question. Mean ratings for each of the questions were averaged per session within each of the emotional categories, yielding seven behavioral variables (Q1: Happy face—happy, Happy face—angry, ambiguous face—happy, ambiguous face—angry, angry face—happy, angry face—angry; Q2; Trust). These stimuli and questions were chosen to assess three levels of emotion perception; ambiguous, non-ambiguous with corresponding cues and ratings (e.g., angry ratings on angry ratings), and non-ambiguous with conflicting cues and ratings (e.g., angry ratings of happy faces).

For the evaluation of the shapes, participants were asked either: (Q1) How yellow is this shape? (anchors: not yellow-very yellow) or How blue is this shape? (anchors: not yellow-very yellow). Q2 was always: How much do you like this color? (anchors: not at all-very much). In the same manner as for ranking the faces, participants were asked to rank their answer on a visual analogue scale (VAS) from 1 to 5, with location of the cursor on the VAS randomized on the presentation of each question.

Brain imaging data was collected on a 3T General Electric Signa HDxt scanner with an 8-channel head coil (GE Healthcare, Milwaukee, Wis., USA).

In the acquisition of MRI data, the protocol included a T2*-weighted gradient echo-planar imaging (EPI) sequence acquired in the transverse plane with the following parameters: Repetition time (TR)=2400 ms, echo time (TE)=30 ms, flip angle (FA)=90°, 64×64 matrix. One run of 528 volumes was collected for each individual in each OT condition (48 slices; in-plane resolution 3.75×3.75 mm; slice thickness 3.2 mm, no gap). A T1-weighted volume, used for co-registration purposes, was acquired using a sagittal fast spoiled gradient echo (FSPGR) sequence with the following parameters: TR=7.8 ms, TE=2.9 ms, FA=12°, 166 slices; in-plane resolution: 1×1, slice thickness: 1.2 mm, 256×256 matrix.

Pupilometry data was collected using an MR-compatible coil-mounted infrared EyeTracking system (NNL EyeTracking Camera®, NordicNeuroLab, Bergen, Norway) at a sampling rate of 60 Hz. Data was recorded using the iView X Software (SensoMotoric Instruments, Teltow, Germany), with a trigger from the stimulus computer syncing the onset of the pupilometry recording to stimulus presentations.

During the experimental sessions, blood samples were collected via IV catheter to assess peripheral levels of OT, AVP, and cortisol at baseline and five time points after the completion of the 20-minute IV administration (0 mins, 10 mins, 30 mins, 60 mins, and 120 mins) throughout the session. Blood samples were centrifuged at 4° C. within 20 minutes of blood draw, after which plasma was frozen at −80° C. until enzyme-linked immunosorbent assay (ELISA) using commercially available kits (Enzo Life Sciences, Farmingdale, N.Y.) was performed using standard techniques (including sample extraction).

Pharmacodynamic Analysis

Analysis was conducted using IBM SPSS Statistics version 22 (IBM Inc.) to determine pharmacokinetics and examine the impact of treatment on outcome measures. A linear mixed-model (LMM) approach was adopted[58], congruent with a recent intranasal crossover psychotropic drug trial[95], for the analysis of emotional expression evaluation, pharmacokinetics, state anxiety, and trustworthiness. All models were fitted using an unstructured matrix. For any significant main effects (i.e., p<0.05), post-hoc tests were performed with the adjustment of critical p values to correct for multiple comparisons using a 5% false discovery rate (FDR)[59].

Experimental treatment was both a fixed and repeated effect in a LMM to assess the impact of treatment on emotion and trustworthiness ratings.

Additionally, in order to investigate the impact of treatment on blood plasma OT, AVP, cortisol concentration and state anxiety a LMM was fitted with 3 fixed factors (treatment, time, treatment×time), 1 repeated factor (treatment). In order to investigate if nasal environments changed between treatment conditions, a repeated measures MANOVA was performed with three dependent variables; MCA, TV0-5, and TV2-5.

Figure 5A:
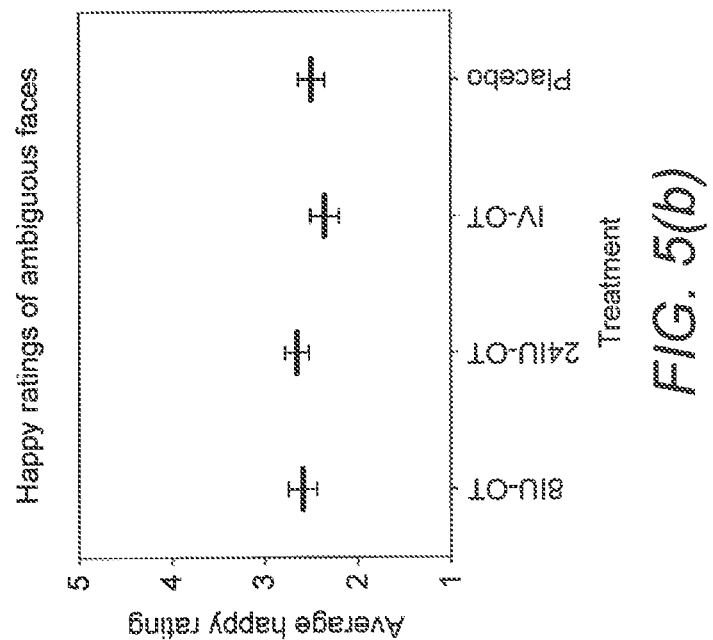
FIGS. 5(a) to (f) represent mean emotional ratings by stimulus, being angry ratings of ambiguous faces (5(a)), happy ratings of ambiguous faces (5(b)), happy ratings of happy faces (5(c)), and ratings of happy faces (5(d)), angry ratings of angry faces (5(e)) and happy ratings of angry faces (5(f)), and treatment, being the intranasal administration of 8 IU of OT (8 IU-OT), the intranasal administration of 24 IU of OT (24 IU-OT), the intravenous delivery of 1 IU of OT (IV-OT), and the intranasal administration of a placebo formulation (Placebo)
Figure 5B:
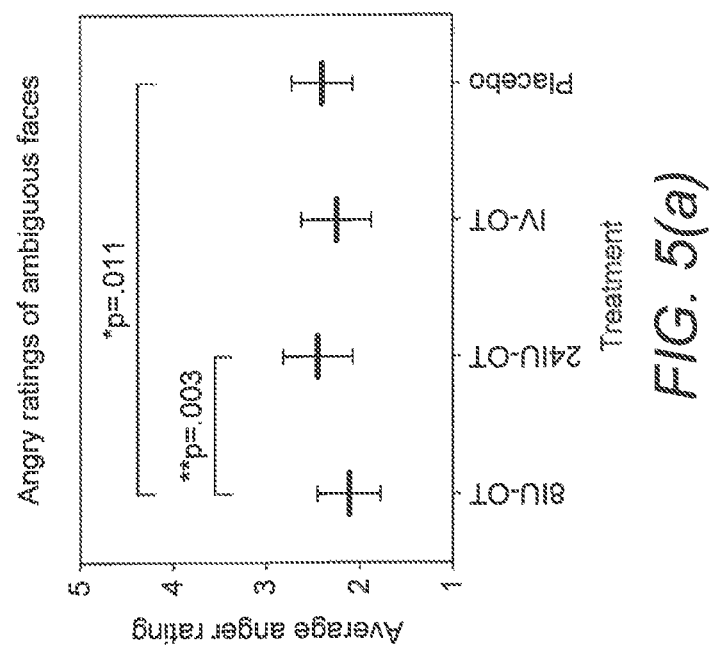
Figure 5D:
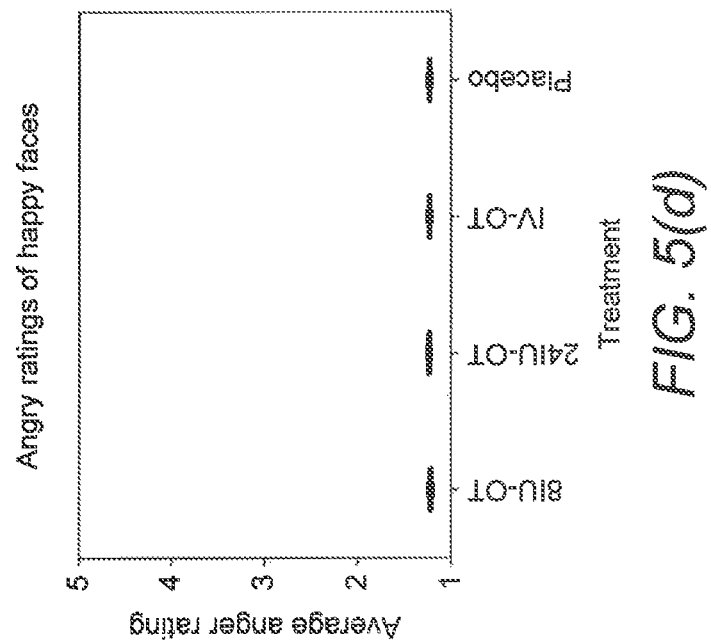
Figure 5C:
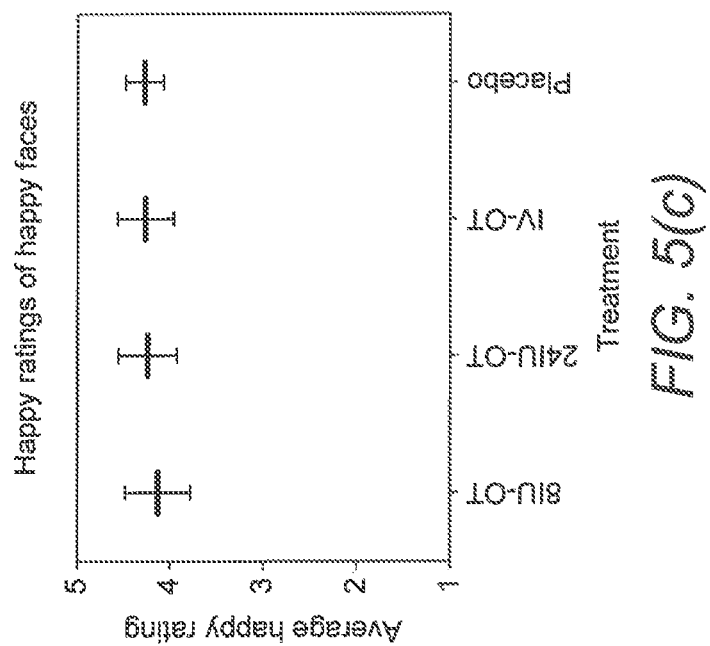
Figure 5F:
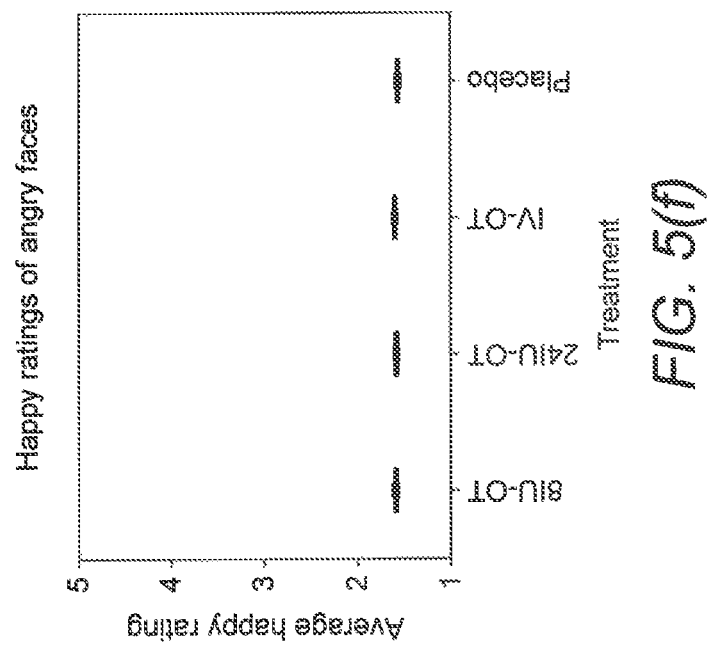
Figure 5E:
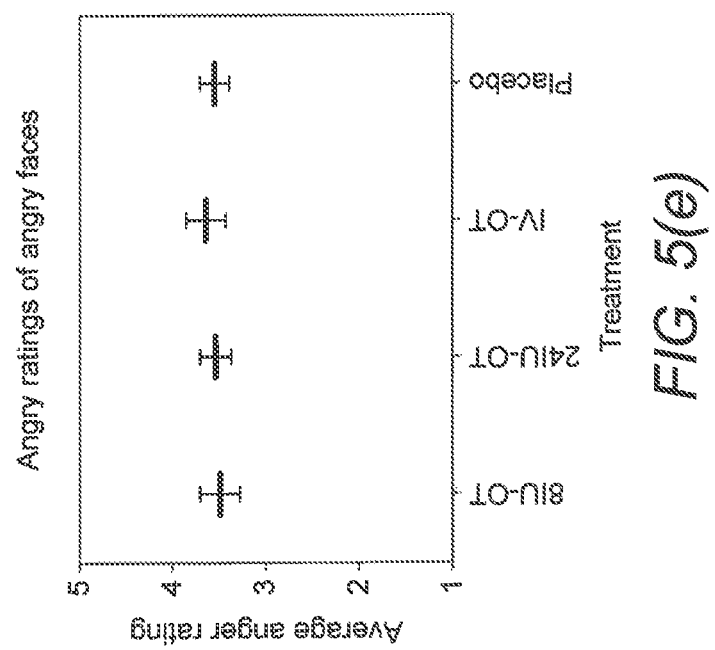

Participant responses to the task are presented in Table 1. Due to equipment difficulties, data was not collected during two (out of sixty-four) testing sessions. A LMM revealed a significant main effect of treatment in the ratings of anger when presented ambiguous faces [F(3,14.72)=7.62, p=0.003; FIG. 5(a)]. Follow-up pairwise comparisons (q=0.05, revised critical value of p<0.017) indicated that angry ratings for ambiguous faces were significantly reduced in the 8 IU-OT treatment condition in comparison to both Placebo (p=0.011; mean decrease=17%, SE decrease 6%) and 24 IU-OT (p=0.003; mean decrease=17%, SE decrease 5%) treatments. There were no main effects of treatment observed for other emotional categories or trustworthiness ratings (FIGS. 5(b) to (f)).

Figures 6A, 6B:
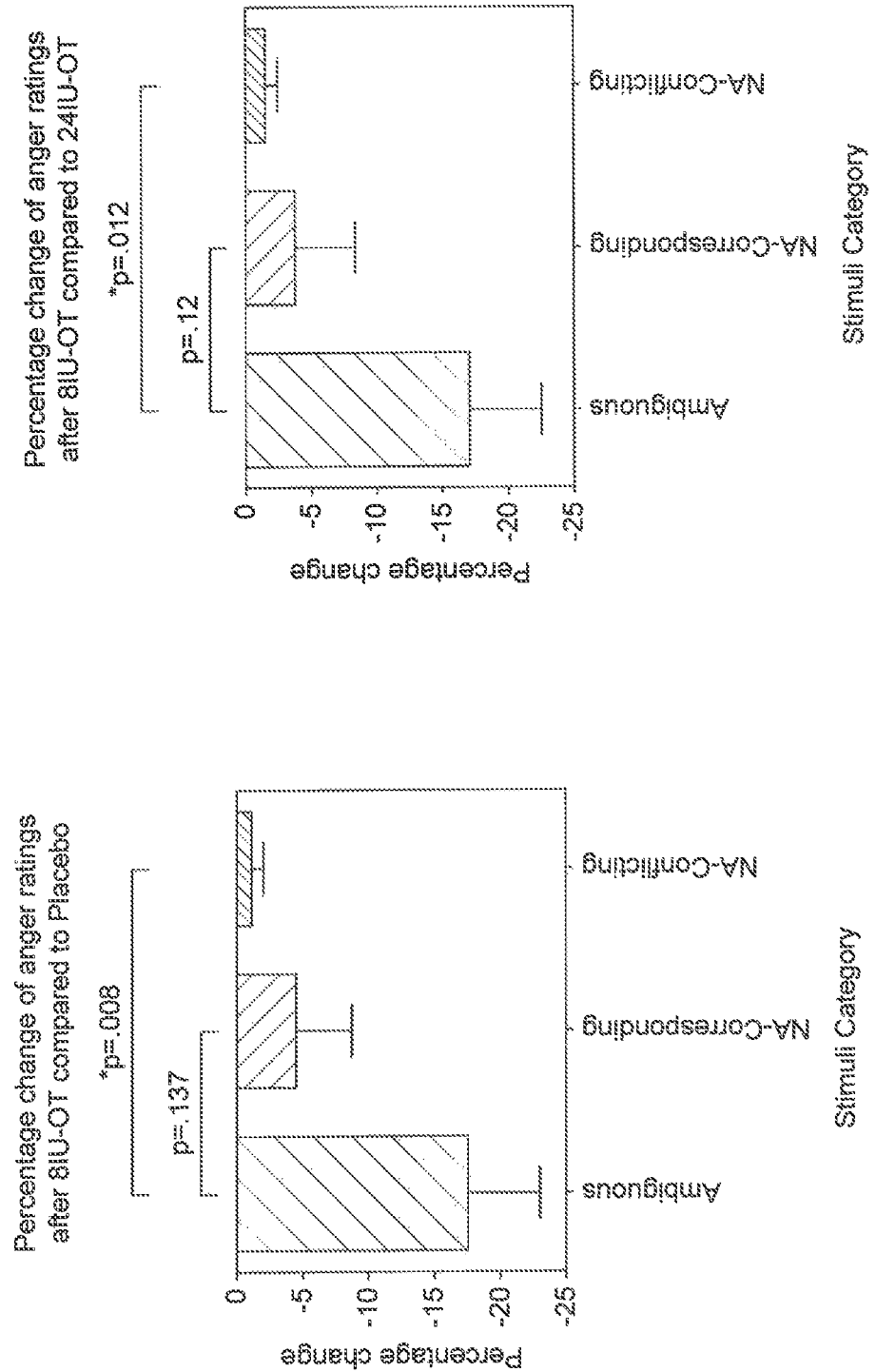
FIG. 6(a) represents the percentage reduction of anger ratings after the 8 IU-OT administration as compared to Placebo by stimuli categories.
FIG. 6(b) represents the percentage reduction of anger ratings after the 8 IU-OT administration as compared to the 24 IU-OT administration by stimuli categories.

For the LMM comparing percentage change between the 8 IU-OT and Placebo treatment, there was a main effect for stimuli type [F(2,14.42)=4.79, p=0.025; FIG. 6(a)]. Follow-up pairwise comparisons to the ambiguous stimuli category (q=0.05, revised critical value of p<0.025) indicated that the percentage reduction of anger ratings of ambiguous stimuli was significantly reduced in comparison to the non-ambiguous (NA)/conflicting stimuli (p=0.012). For the LMM comparing percentage change between the 8 IU-OT and 24 IU-OT treatment, there was a main effect for stimuli type [F(2,14.05)=7.01, p=0.007; FIG. 6(b)]. Follow-up pairwise comparisons to the ambiguous stimuli category (q=0.05, revised critical value of p<0.025) indicated that the percentage reduction of anger ratings of ambiguous stimuli was significantly reduced in comparison to the non-ambiguous/conflicting stimuli (p=0.008).

Out of 384 possible data points, 19 OT, 26 AVP, and 18 cortisol plasma concentration assessments were excluded due to technical issues relating to blood sample collection or analysis.

Oxytocin Blood Plasma Concentration:

The mean OT plasma concentrations over time after the administration of 8 IU-OT, 24 IU-OT, IV-OT and Placebo (with error bars representing standard error of the mean) are represented in Table 2 and FIG. 7(a). For the 4 (treatment)×6 (time) LMM, there was a significant main effect of treatment on OT blood plasma concentration [F(3,88.71)=4.25, p=0.007]. Follow-up pairwise comparisons (q=0.05, revised critical value of p<0.025) revealed that plasma OT concentration was significantly increased in the IV-OT (p=0.009),

TABLE 1

Participant ratings in the social cognition task

| Outcomes | | | | | Linear mixed model main effect | | |
|---|---|---|---|---|---|---|---|
| Emotional expression evaluation | 8IU-OT | 24IU-OT | IV-OT | Placebo | df | F | p |
| Angry ratings of ambiguous faces | 2.11 (0.15) | 2.46 (0.17) | 2.32 (0.16) | 2.41 (0.15) | 3, 14.72 | 7.62 | 0.003 |
| Happy ratings of ambiguous faces | 2.61 (0.14) | 2.67 (0.12) | 2.36 (0.14) | 2.51 (0.13) | 3, 15.17 | 1.78 | 0.193 |
| Angry ratings of angry faces | 3.51 (0.2) | 3.54 (0.18) | 3.68 (0.2) | 3.57 (0.16) | 3, 14.76 | 0.82 | 0.505 |
| Happy ratings of angry faces | 4.15 (0.62) | 4.26 (0.57) | 4.29 (0.54) | 4.3 (0.36) | 3, 15 | 0.32 | 0.314 |
| Angry ratings of happy faces | 1.23 (0.02) | 1.25 (0.02) | 1.24 (0.02) | 1.24 (0.02) | 3, 15 | 0.97 | 0.433 |
| Happy ratings of happy faces | 4.11 (0.16) | 4.26 (0.14) | 4.31 (0.13) | 4.3 (0.09) | 3, 13.84 | 1.32 | 0.305 |
| Trustworthiness | 3.13 (0.04) | 3.15 (0.05) | 3.16 (0.05) | 3.11 (0.03) | 3, 14.27 | 2.57 | 0.095 |

Note.
Unless specified otherwise, values are estimated means based on linear mixed models with standard error in parenthesis.

In order to evaluate the specificity of the effect for ambiguous faces (vs. non-ambiguous faces with corresponding cues and non-ambiguous with conflicting cues), a percentage change score was calculated comparing ratings after 8 IU-OT and Placebo treatments, and comparing 8 IU-OT with 24 IU-OT treatments (i.e., the treatment comparisons that demonstrated significant differences in emotional ratings). Ambiguous=anger ratings of ambiguous faces; NA—corresponding=Anger ratings of non-ambiguous faces with corresponding cues; NA—conflicting=Anger ratings of non-ambiguous faces with conflicting cues. Stimuli category was both a fixed and repeated effect in a LMM to assess the impact of stimuli category on the reduction of anger ratings.

8 IU-OT (p=0.001), and 24 IU-OT (p=0.002) treatments compared to the Placebo treatment. None of the other pairwise comparisons reached significance. There was also a significant main effect for time [F(5,90.29)=5.93, p<0.001], with follow-up pairwise analyses (q=0.05, revised critical value of p<0.017) indicating significantly increased plasma OT immediately after IV administration in comparison to baseline (p<0.001), 10 minutes (p=0.01), 30 minutes (p=0.001), 60 minutes (p=0.001), and 120 minutes after the completion of IV administration (p<0.001). There was no significant condition×time interaction, F(15,88.69)=1, p=0.461.

TABLE 2

| | 8IU-OT | | | 24IU-OT | | | IV-OT | | | Placebo | | |
|---|---|---|---|---|---|---|---|---|---|---|---|---|
| Time | Mean | SEM | N | Mean | SEM | N | Mean | SEM | N | Mean | SEM | N |
| −20 | 4.59 | 1.08 | 16.00 | 7.72 | 2.40 | 15.00 | 6.02 | 1.55 | 16.00 | 3.95 | 0.45 | 15.00 |
| 0 | 6.88 | 1.43 | 15.00 | 14.20 | 3.64 | 14.00 | 25.64 | 3.98 | 16.00 | 5.14 | 1.18 | 14.00 |
| 10 | 8.29 | 2.90 | 14.00 | 11.98 | 2.81 | 15.00 | 10.79 | 2.75 | 15.00 | 4.25 | 0.66 | 15.00 |
| 30 | 9.88 | 3.63 | 16.00 | 8.47 | 1.96 | 15.00 | 6.99 | 1.77 | 16.00 | 5.26 | 1.39 | 14.00 |
| 60 | 9.76 | 2.63 | 16.00 | 7.70 | 1.98 | 16.00 | 9.50 | 2.44 | 14.00 | 5.02 | 1.06 | 15.00 |
| 120 | 8.64 | 2.22 | 16.00 | 6.31 | 1.19 | 16.00 | 6.13 | 1.09 | 16.00 | 5.39 | 1.63 | 15.00 |

Figure 7B:
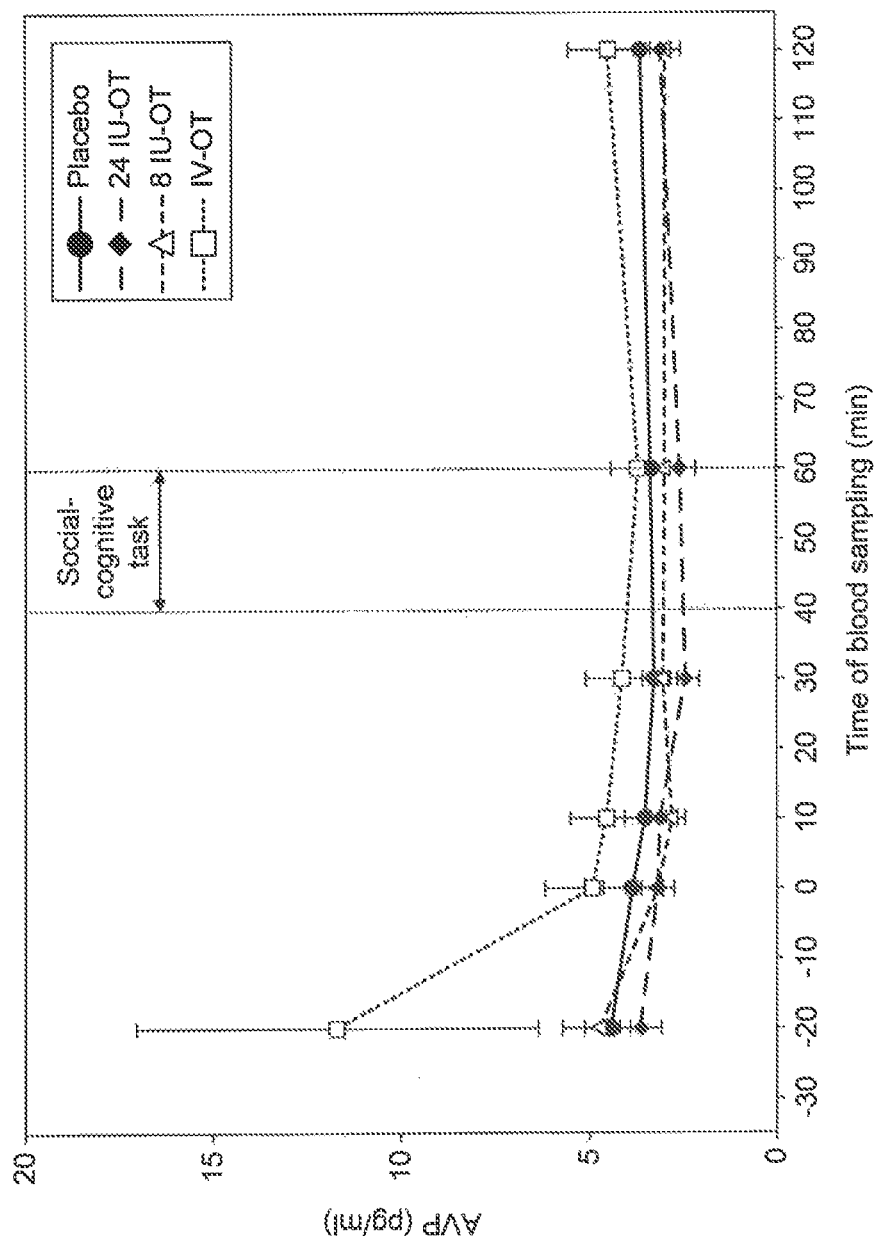
FIG. 7(b) represents the mean vasopressin (AVP) plasma concentration over time after the administrations of 8 IU-OT, 24 IU-OT, IV-OT and Placebo, with error bars representing standard error of the mean.

Vasopressin Blood Plasma Concentration:

The mean AVP plasma concentrations over time after the administration of 8 IU-OT, 24 IU-OT, IV-OT and Placebo (with error bars representing standard error of the mean) are represented in Table 3 and FIG. 7(b). For the 4 (treatment)×6 (time) LMM, there was a significant main effect of treatment on AVP blood plasma concentration [$F(3,82.42)=4.55$, $p=0.005$]. Follow-up pairwise comparisons ($q=0.05$, revised critical value of $p<0.0083$) revealed plasma AVP concentration was significantly decreased after 24 IU-OT treatment in comparison to Placebo treatment ($p=0.008$) and IV-OT ($p=0.013$), and significantly decreased after 8 IU-OT treatment in comparison to IV-OT ($p=0.023$). There was no significant main effect of time [$F(5,90.63)=1.81$, $p=0.12$] or treatment×time interaction, $F(15,82.46)=1.03$, $p=0.434$.

TABLE 3

| | 8IU-OT | | | 24IU-OT | | | IV-OT | | | Placebo | | |
|---|---|---|---|---|---|---|---|---|---|---|---|---|
| Time | Mean | SEM | N | Mean | SEM | N | Mean | SEM | N | Mean | SEM | N |
| −20 | 4.76875 | 0.9233417 | 16 | 3.578571 | 0.5601391 | 14 | 11.72 | 5.314878 | 15 | 4.366667 | 0.7328786 | 15 |
| 0 | 3.185715 | 0.4818528 | 14 | 3.128571 | 0.46639 | 14 | 4.906667 | 1.317554 | 15 | 3.86 | 0.707228 | 14 |
| 10 | 2.876923 | 0.4643929 | 13 | 3.107143 | 0.4459173 | 14 | 4.471428 | 1.028999 | 14 | 3.49375 | 0.5508682 | 16 |
| 30 | 3.0875 | 0.4738033 | 16 | 2.471428 | 0.3692029 | 14 | 4.085714 | 0.9966899 | 14 | 3.266667 | 0.5889996 | 15 |
| 60 | 3.08125 | 0.4533412 | 16 | 2.62 | 0.408155 | 15 | 3.653333 | 0.7655603 | 15 | 3.38125 | 0.5472826 | 16 |
| 123 | 3.0875 | 0.4865589 | 16 | 3.126667 | 0.5076056 | 15 | 4.52 | 1.10122 | 15 | 3.65625 | 0.7101625 | 16 |

Figure 7C:
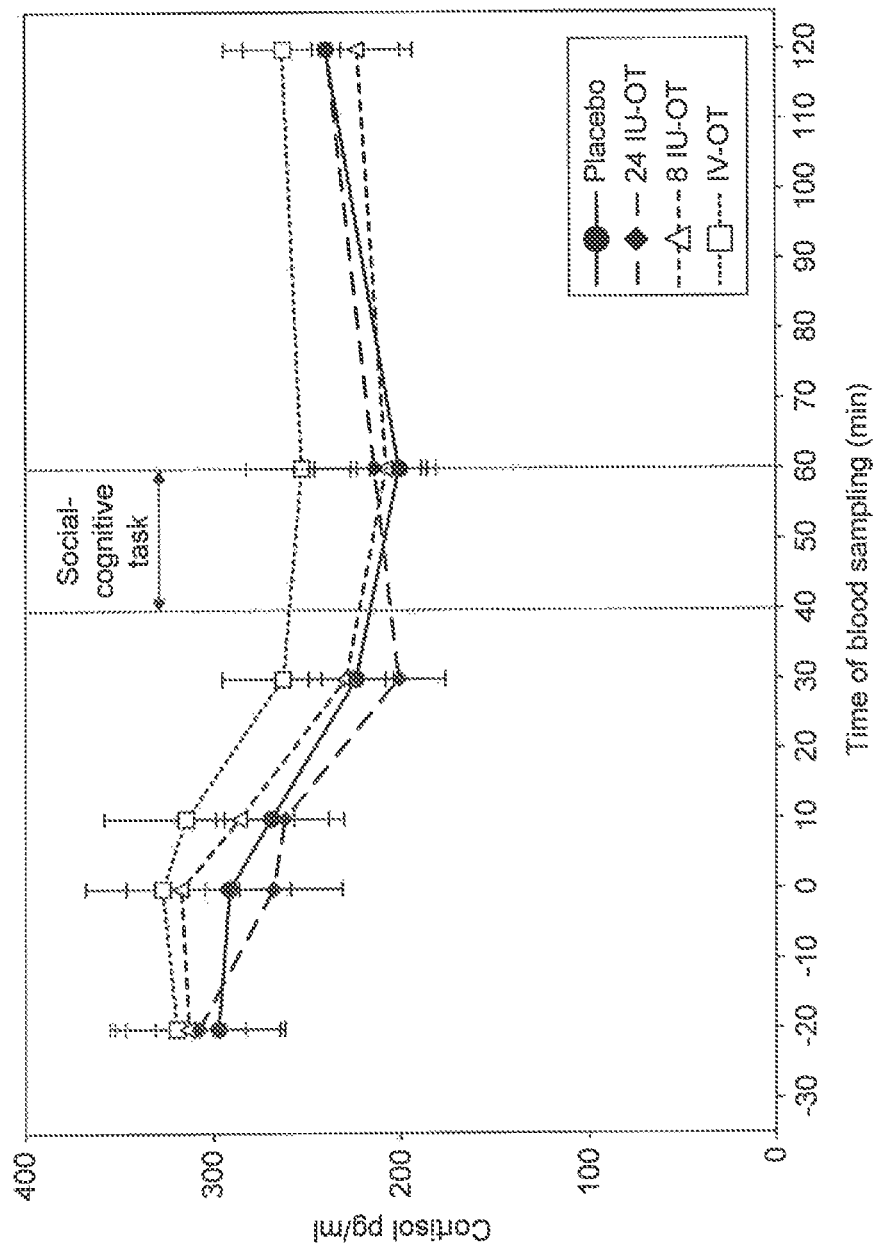
FIG. 7(c) represents the mean cortisol plasma concentration over time after the administrations of 8 IU-OT, 24 IU-OT, IV-OT and Placebo, with error bars representing standard error of the mean.

Cortisol Blood Plasma Concentration:

The mean cortisol plasma concentrations over time after the administration of 8 IU-OT, 24 IU-OT, IV-OT and Placebo (with error bars representing standard error of the mean) are represented in Table 4 and FIG. 7(c). For the 4 (treatment)×6 (time) LMM there was a significant main effect of treatment on cortisol blood plasma concentration [$F(3,84.77)=4.82$, $p=0.004$]. Follow-up pairwise comparisons ($q<0.05$, revised critical value of $p<0.017$) revealed significantly increased cortisol concentration following IV-OT treatment compared to Placebo treatment ($p=0.01$) and 24 IU-OT ($p<0.001$), but not 8 IU-OT. There was a significant main effect of time on cortisol blood plasma concentration [$F(5,90.07)=2.4$, $p=0.04$], but no significant follow-up pairwise comparisons were found. Finally, there was no significant treatment×time interaction [$F(15,84.72)=0.421$, $p=0.969$].

TABLE 4

| | 8IU-OT | | | 24IU-OT | | | IV-OT | | | Placebo | | |
|---|---|---|---|---|---|---|---|---|---|---|---|---|
| Time | Mean | SEM | N | Mean | SEM | N | Mean | SEM | N | Mean | SEM | N |
| −20 | 315.1875 | 32.40695 | 16 | 307.6429 | 45.70012 | 14 | 319.1875 | 36.74906 | 16 | 297.66677 | 33.23934 | 15 |
| 0 | 317.9375 | 28.85834 | 16 | 268.1429 | 36.8121 | 14 | 327.2667 | 41.42928 | 15 | 291.4 | 32.17849 | 15 |
| 10 | 286.3077 | 28.85605 | 18 | 262.2852 | 31.79837 | 14 | 315.2 | 43.45257 | 15 | 268.875 | 29.88253 | 16 |
| 30 | 229.125 | 20.52171 | 16 | 201.4268 | 24.05185 | 14 | 263.25 | 32.14855 | 16 | 223.8 | 19.33765 | 15 |
| 60 | 208.625 | 18.48893 | 16 | 214.4 | 32.12739 | 15 | 253 | 29.17333 | 16 | 201.875 | 14.89851 | 16 |
| 120 | 224.375 | 23.2185 | 16 | 239.4667 | 44.85382 | 15 | 263.875 | 31.46703 | 16 | 239.9375 | 18.17449 | 16 |

In this study, it has been demonstrated that 8 IU-OT treatment reduces the perception of anger in emotionally ambiguous facial stimuli with minimal systemic exposure. Importantly, the current findings are the first to suggest that a low dose of OT is more effective than a higher dose in modulating social cognition. Moreover, these results provide behavioral evidence that OT delivered intranasally using the delivery device of this study reaches the brain and influences social cognition, whereas peripherally administered OT, which similarly increased plasma OT concentration, had no such effect.

This data highlights the subtle effect of OT on the processing of emotionally ambiguous facial stimuli in relation to anger perception, as there was no difference in the ratings of angry or happy faces. Whereas the specific effects of OT in the emotionally ambiguous stimuli indicate that OT only influences the emotional assessment of stimuli which are non-abundant with overt cues, the lack of effects in the happy and angry stimuli could also be explained by the relatively low variability in ratings of these stimuli. Notably, there were also no differences in ratings of trust between the placebo condition and any of the OT conditions. While this may have been due to the explicit nature of the "trust" question [most research has used more nuanced economic tasks[64]], this adds to mounting evidence that OT may not increase the perception of trustworthiness[96-97].

The present delivery regime, which provides for efficacy with lower dose concentrations, also has a particular advantage of enabling regulation of the balance of OT and AVP concentrations[49] via cross-reactivity with AVP receptors[50,98-100]. In addition, compared to higher doses, lower doses have been shown to increase peripheral levels of OT in saliva[65], attenuate cortisol stress responses[66], and increase eye gaze in patients with Fragile X syndrome[67]. Furthermore, a low dose of OT administered shortly after birth has been shown to increase partner preference later in life[68]. Similarly, lower doses have been associated with stronger increases in social recognition compared to higher doses[69-70].

Much like OT, AVP receptors are located both centrally and peripherally[74-75] and play an important role in social behavior and psychopathology[49]. It is postulated that this "off target" activity may contribute to a non-linear dose-response and further highlights the importance of establishing the dose regimen that optimizes therapeutic effects[101].

Importantly, the present dose-response data provides evidence to the optimal dose for social cognition modulation, demonstrating that a lower dose is more likely to modulate social cognition than a higher dose. Furthermore, patients with underlying deficits responsive to OT, may respond more robustly than healthy volunteers.

The present data on the perception of facial stimuli is generally consistent with results from past studies in humans, particularly negatively valenced emotions[81], as differences were only discovered on the perception of anger in emotionally ambiguous faces. These results documenting specifically reduced negativity bias for emotionally ambiguous faces have important implications for disorders that are characterized by a negative bias towards social stimuli (e.g., social anxiety disorder). Prior studies suggest that OT reduces bias towards negative information in clinically anxious[82] and high trait anxious individuals[83]; however, this is the first study to the present Inventors' knowledge to report data suggesting a reduction of negativity bias in healthy individuals.

Nasal Valve Dimension Analysis

Analysis was conducted using the R statistical package (version 3.1.1; R Development Core Team, 2014) to examine the role of the cross-sectional area of the nasal valve, being the slit-like structure at the junction between the anterior and posterior regions of each nasal cavity, on pharmacodynamics. A repeated-measures ANOVA was first conducted to investigate if the cross-sectional area of the nasal valve significantly fluctuated from session-to-session (screening session and each treatment session). Additionally, as the cross-sectional area may differ according to an individuals' overall size and age, Pearson correlation coefficients were calculated to assess the relationship between these factors at the time of screening.

The correlation between the response to angry ambiguous faces and the mean cross-sectional area of the nasal valve was determined after 8 IU-OT, 24 IU-OT, IV-OT and Placebo treatments. In this study, as administration was done to both the left and right nasal cavities, the mean cross-sectional areas were determined for each of the left and right nasal cavities, and a mean cross-sectional area was determined from the sum of these means for the left and right nasal cavities.

TABLE 5A

Mean cross-sectional area of nasal valve for left nasal cavity

|  | Mean | SEM | N |
| --- | --- | --- | --- |
| Screening | 0.664 | 0.056 | 16 |
| 8IU-OT | 0.609 | 0.045 | 16 |
| 24IU-OT | 0.676 | 0.056 | 16 |
| IV-OT | 0.631 | 0.044 | 16 |
| Placebo | 0.746 | 0.091 | 16 |

TABLE 5B

Mean cross-sectional area of nasal valve for right nasal cavity

|  | Mean | SEM | N |
| --- | --- | --- | --- |
| Screening | 0.599 | 0.062 | 16 |
| 8IU-OT | 0.619 | 0.058 | 16 |
| 24IU-OT | 0.614 | 0.064 | 16 |
| IV-OT | 0.617 | 0.060 | 16 |
| Placebo | 0.561 | 0.052 | 16 |

TABLE 5C

Mean cross-sectional area of nasal valve as determined from the sum of mean cross-sectional are of nasal valves of left and right nasal cavities

|  | Mean | SEM | N |
| --- | --- | --- | --- |
| Screening | 0.632 | 0.046 | 16 |
| 8IU-OT | 0.614 | 0.035 | 16 |
| 24IU-OT | 0.645 | 0.042 | 16 |
| IV OT | 0.624 | 0.04 | 16 |
| Placebo | 0.654 | 0.049 | 16 |

Bayes Factors using the Jeffreys-Zellner-Slow method[60] were also calculated to assess the strength of evidence for the null and alternative hypotheses. This approach is especially useful in determining if the data supports the null hypotheses (i.e., no relationship between two variables) over the alternative hypothesis (i.e., there is a relationship between two variables), as a non-significant p-value is unable to provide evidence for the null-hypothesis[85]. A Bayes value less than ⅓ provides substantial evidence for the null hypothesis, over 3 provides strong evidence for the alternative hypothesis, and between ⅓ and 3 provides no strong support either way[63].

Confidence intervals for the difference between correlations for each treatment condition were calculated to compare the strength of correlation to investigate whether the relationship between the mean cross-sectional area of the nasal valve and anger ratings of ambiguous faces is significantly greater than the relationships observed after the other treatments. As these variables are highly related due to measurements being taken from the same sample[62], the CIs were adjusted to account for overlap[58] using the Fisher Z transformation. Any CI interval that includes zero would indicate that the null hypothesis of no difference between the correlations could not be rejected.

The relationship between blood plasma and the mean cross-sectional area of the nasal valve was also calculated, as represented in Table 6. A change score between baseline OT and AVP and serum levels just before the social cognition assessment (~40 minutes after treatment) was calculated to explore the effect of the cross-sectional area of the nasal valve on OT, AVP and cortisol on systemic availability.

In addition, there was no relationship between the cross-sectional area of the nasal valve and plasma concentration of OT, AVP, or cortisol after any of the treatment conditions.

The present study evidences that the efficacy of OT on social cognition can be influenced by control of the cross-sectional area of the nasal valve when intranasally administering a defined, lower-dosage of OT less than 24 IU. In one embodiment this control is obtained by the effective pressure of the exhaled air flow and the structural effect of the nosepiece in opening the nasal valve.

fMRI Analysis

Conventional fMRI pre-processing of the fMRI data was performed using independent component analysis (ICA) and auto-classification using the FMRIB's ICA-based X-noiseifier (FIX) method in order to de-noise the fMRI data.

The Individual components were grouped using a temporal concatenation approach in MELODIC (Multivariate Exploratory Linear Optimised Decomposition Into Independent Components), fixed model order at 40 components.

The component with strongest amygdala weighting (and also having strong medial temporal lobe (MTL) and brain stem weighting) was then determined, here Independent Component #37 (IC0037).

TABLE 6

The relationship between mean cross-sectional area or the nasal valve and plasma concentration of oxytocin, vasopressin, and cortisol

| | BTU-OT | | | | 24IU-OT | | | | IV-OT | | | | Placebo | | | |
|---|---|---|---|---|---|---|---|---|---|---|---|---|---|---|---|---|
| | r | 95 % CI | n | p | r | 95 % CI | n | p | r | 95 % CI | n | p | r | 95 % CI | n | p |
| Plasma OT | .13 | −.39, .59 | 15 | .63 | 0.2 | −.39, .68 | 12 | 0.51 | −0.1 | −.56, .42 | 15 | .73 | .35 | −.2, .73 | 14 | .21 |
| Plasma AVP | .02 | −.48, .51 | 15 | .95 | 0.4 | −.19, .78 | 12 | 0.17 | .19 | −.38, .65 | 13 | .52 | .38 | −.19, .76 | 13 | .18 |
| Plasma cortisol | .14 | −.38, .6 | 15 | .59 | .29 | −.31, .72 | 12 | .34 | −.22 | −.64, .31 | 15 | .42 | −.07 | −.58, .47 | 13 | .8 |

A repeated-measures ANOVA revealed no main effect of time for the mean cross-sectional area of the nasal valve [$F(1.99, 29.86) = 0.69$, $p = 0.51$; $\eta^2_p = 0.044$]. There was also no relationship between age [$r = 0.56$, 95% CI (−0.45, 0.54), $n = 16$, $p = 0.84$] and BMI [$r = −0.68$, 95% CI (−0.55, 0.44), $n = 15$, $p = 0.015$] with the mean cross-sectional area of the nasal valve at the time of screening.

The calculation of Pearson correlation coefficients revealed a significant relationship between the anger ratings of neutral faces and the mean cross-sectional area of the nasal valve after 8 IU-OT treatment [$r = −0.61$, 95% CI (−0.85, −0.14), $n = 15$, $p = 0.015$], with a corresponding Bayes factor (B) of 3.62, representing substantial evidence that these two variables are related. The relationship between angry ratings of ambiguous faces and the mean cross-sectional area of the nasal valve following the 8 IU-OT treatment is represented in FIG. 8.

Figure 8:
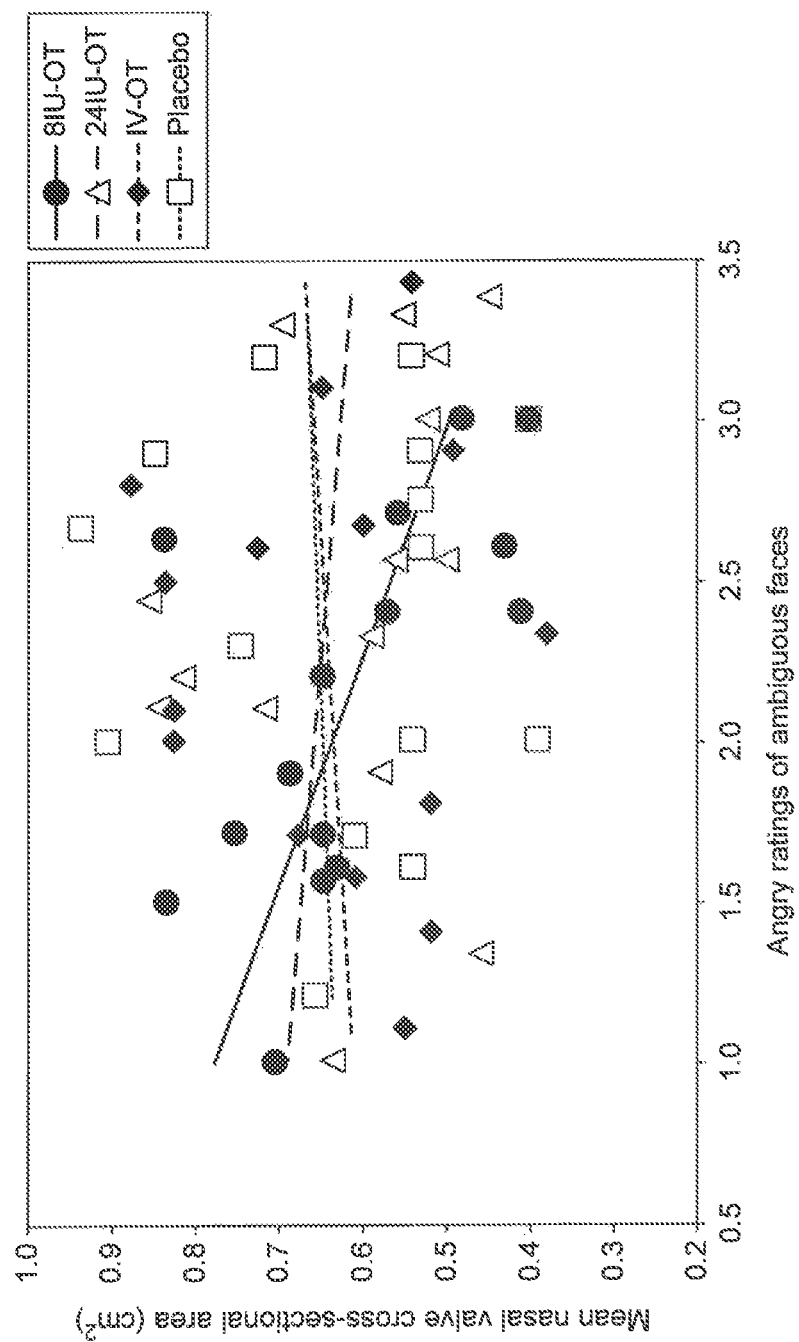
FIG. 8 illustrates the relationship between the mean nasal valve cross-sectional area and angry ratings of neutral faces by subjects after the administrations of 8 IU-OT, 24 IU-OT, IV-OT and Placebo.

As represented in FIG. 8, there was no relationship between treatment and anger ratings of neutral faces after 24 IU-OT treatment [$r = −0.14$, 95% CI (−0.59, 0.38), $n = 16$, $p = 0.6$; $B = 0.22$], IV-OT [$r = 0.11$, 95% CI (−0.43, 0.59), $n = 15$, $p = 0.7$; $B = 0.21$], or Placebo [$r = 0.04$, 95% CI (−0.46, 0.53), $n = 16$, $p = 0.88$; $B = 0.19$] treatment, with all respective Bayes factors indicative of substantial evidence that these variables are not related to each other.

A comparison of the correlation coefficients also revealed a significant difference between the correlations of the 8 IU-OT, and IV [$r = −0.72$ (−1.4, −0.2)] and Placebo [$r = −0.65$ (−1.1, −0.06)] treatments, but no significant difference in the correlation with 24 IU-OT treatment [$r = −0.42$ (−0.97, 0.06)].

Figures 9A, 9B, 9C:
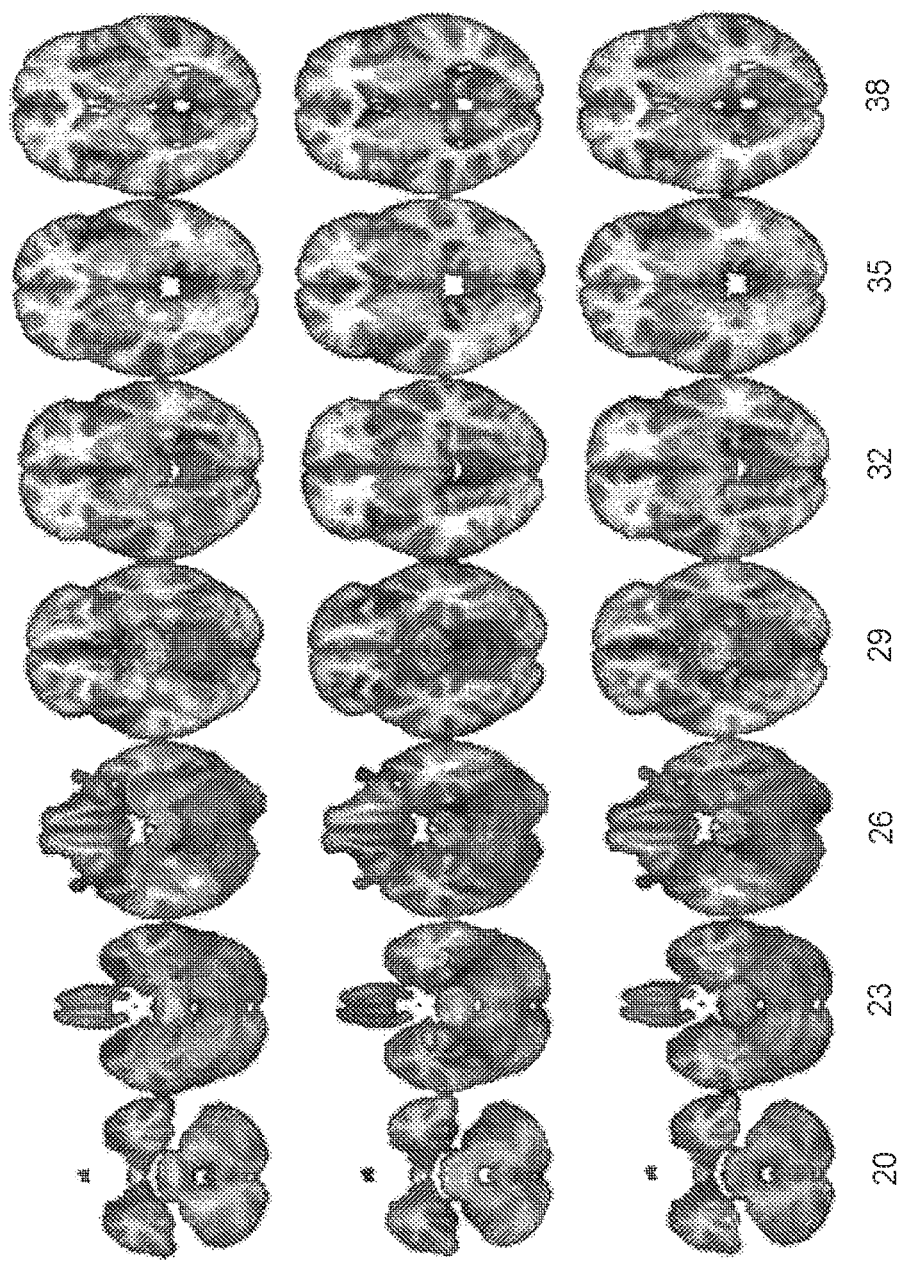
FIG. 9(a) illustrates time-course spatial maps determined from fMRI analysis for Independent Component #37 showing strong amygdala, medial temporal lobe (MTL) and brain stem weighting.
FIG. 9(b) illustrates time-course spatial maps of the two largest clusters (voxel-wise p<0.01, uncorrected) in Independent Component #37, which are localized within the left and right amygdala, respectively.
FIG. 9(c) illustrates time-course spatial maps of the two largest clusters showing significantly (p<0.05, cluster size corrected using permutation testing) increased connectivity in the 8 IU-OT treatment as compared to Placebo in the left and right amygdala, respectively.

Dual regression was then performed to estimate the spatial maps of the individual components and the corresponding time courses, as represented in FIG. 9(a), which reflects one sample t-tests across all datasets (t>5) after dual regression.

Voxel-wise general linear model (GLM) testing was performed for evaluation of the main effect of the OT condition (F-test across the IU08-OT, IU24-OT, IV-OT and Placebo treatments) on the individual spatial maps within the canonical component (t>5) for IC0037. The largest clusters at voxel-wise p<0.01, uncorrected, were then identified. The two largest clusters showing the main effects of the OT condition are localized within the left and right amygdala, respectively, as represented in FIG. 9(b).

Next, pairwise comparison between 8 IU-OT and Placebo treatments revealed two clusters showing significantly (p<0.05, cluster size corrected using permutation testing) increased connectivity in the 8 IU-OT treatment as compared to Placebo in the left and right amygdala, respectively, as represented in FIG. 9(c). The mean connectivity value for each dataset in each of these four clusters was extracted and submitted to further analysis (here in MATLAB).

Figure 10A:
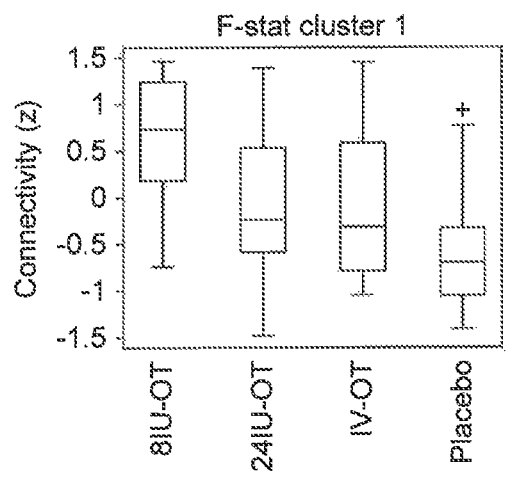
FIGS. 10(a) and (b) illustrate boxplots of the mean connectivity within the two clusters from fMRI analysis showing significant (p<0.01, uncorrected) main effects of the OT condition.
Figure 10B:
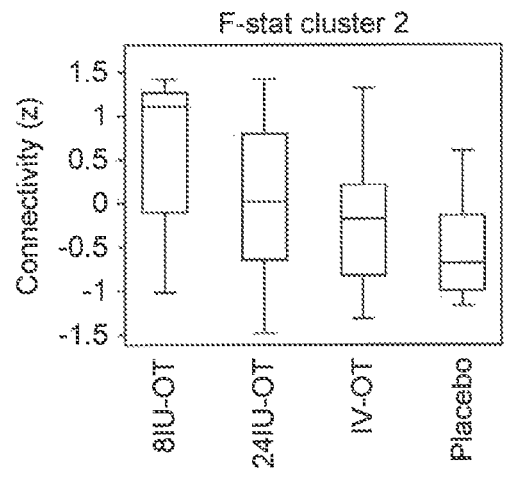
Figure 11A:
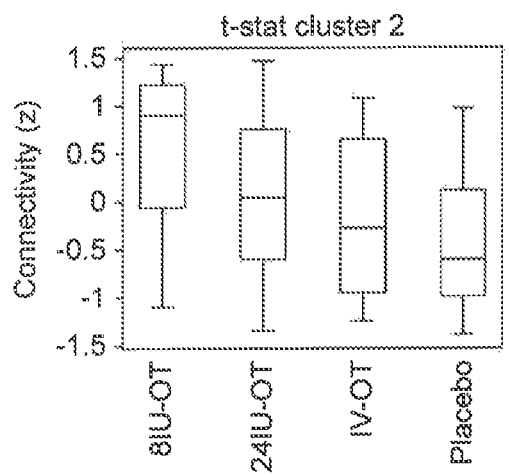
FIGS. 11(a) and (b) illustrate boxplots of the mean connectivity within the two clusters from fMRI analysis showing significantly (p<0.05, cluster size corrected) Increased connectivity after the 8 IU-OT and Placebo treatments.
Figure 11B:
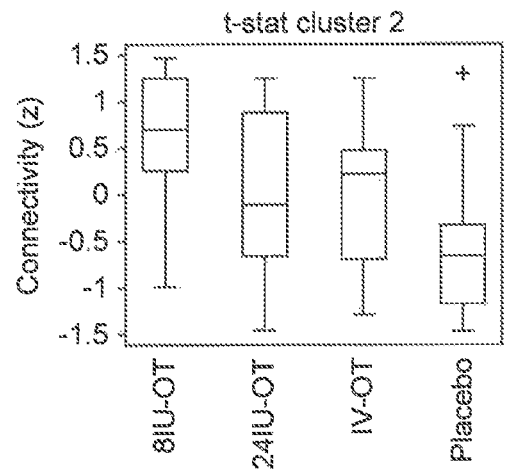

A repeated-measures ANOVA was performed. FIGS. 10(a) and (b) illustrate boxplots of the mean connectivity within the two clusters showing significant (p<0.01, uncorrected) main effects of the OT condition. FIGS. 11(a) and (b) illustrate boxplots of the mean connectivity within the two clusters showing significantly (p<0.05, cluster size corrected) increased connectivity after the 8 IU-OT and Placebo treatments. The connectivity values are normalized (z scores) relative to each subject's mean value across conditions in order to ease comparison).

Figure 12A:
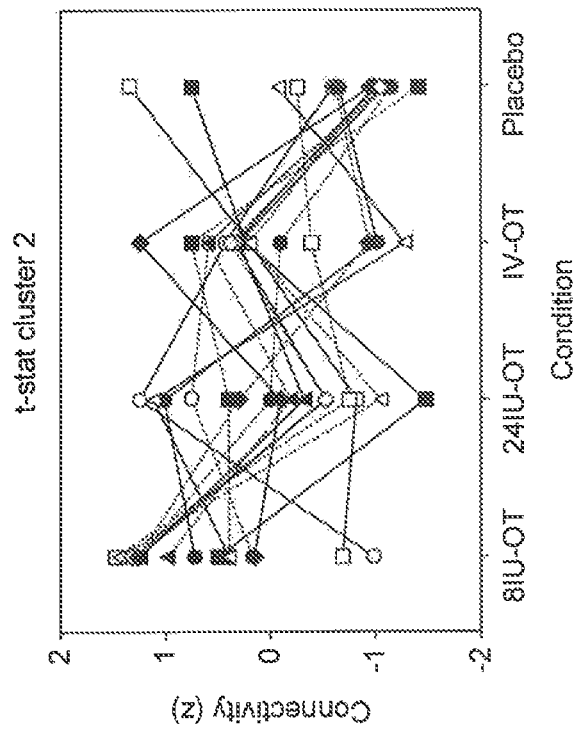
FIGS. 12(a) and (b) represent, by way of spaghetti plots, the connectivity values in all conditions in each of the significant amygdala clusters obtained from the pairwise comparison of the 8 IU-OT and Placebo treatments for each individual.
Figure 12B:
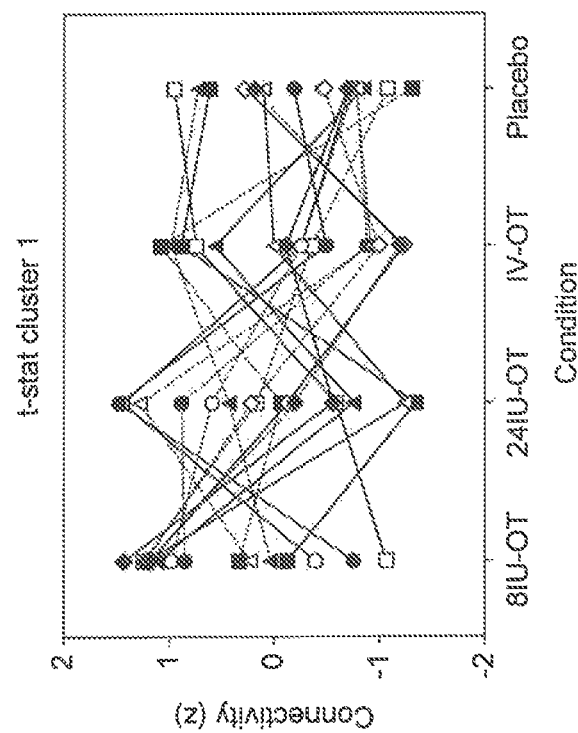

FIGS. 12(a) and (b) represent, by way of spaghetti plots, the connectivity values in all conditions in each of the significant amygdala clusters obtained from the pairwise comparison, as illustrated in FIG. 9(c), for each individual.

As expected, repeated-measures ANOVA revealed significant main effects of condition in both clusters (p=0.0032 and p=0.0039). Boxplots suggest that main effects of OT condition are driven by IU08-OT vs Placebo, indicating increased amygdala connectivity in the IU08-OT treatment, which is also supported by post-hoc pairwise comparisons (t=−2.54, p=0.016, and t=−2.24, p=0.033).

The amygdala is a key brain region for emotion regulation[86], playing an important role in processing incoming social stimuli[87]. Indeed, converging neuroimaging evidence suggests the amygdala is an important target of OT administration. For instance, a single administration of intranasal OT has been reported to both decrease[88-89] and increase[90-91] amygdala activity when viewing a range of emotional stimuli. While these early studies measured neuronal recruitment during the presentation of stimuli, recent work has begun to explore brain activity at rest. It is reported that the amygdala is a key constituent of a larger "social brain network" that displays increased blood flow after OT administration[92]. Similarly, data indicates that OT administration increases connectivity between the amygdala and the rostral medial frontal cortex[93].

The present study is the first to examine resting state connectivity after OT administration of different doses (8 IU and 24 IU) and treatment modalities (intranasal vs. Intravenous). The data suggests that a low dose of OT delivered intranasally (but not intravenously) modulates amygdala connectivity, which is consistent with nose-to-brain delivery. Increased amygdala connectivity may facilitate the increased salience of social stimuli, which is suggested to underpin the observed effects of OT on social cognition and behavior[10]. These results may also have implications for the treatment of psychiatric disorders characterized by social impairment, which are also reported to have abnormal coupling between the amygdala and other brain regions (e.g., schizophrenia)[94]. Moreover, the data also adds to our understanding of how different OT doses and administration modalities influence neuronal recruitment at rest.

In summary, the present study presents new insights in relation to an improved method of deep intranasal OT delivery, and shows that greater pharmacodynamic activity can be shown specifically using the present delivery regime of OT as compared to IV delivery producing similar systemic exposure, suggesting that direct nose-to-brain activity is being achieved. This data also provides preliminary evidence that the selection of intranasal OT dose based on precedence, rather than experimental evidence, may be misguided; the current study indicating that a lower dose (8 IU) can offer greater efficacy than a higher dose (24 IU) when suitably administered.

MRI and Pupilmetry Analysis

FreeSurfer (http://surfer.nmr.mgh.harvard.edu) was used for of the T1-weighted data, including surface reconstruction and full brain segmentation[123] to obtain precise brain extracted volumes for co-registration of the fMRI data. FRRIB Software Library (FSL; http://fsl.fmrib.ox.ac.uk/fsl/fslwiki/[124]) was used to process fMRI data. The first five volumes were discarded. Pre-processing of fMRI data was conducted using FMRIB's Expert Analysis Tool (FEAT) version 6.0128. This included motion correction using MCFLIRT[124], spatial smoothing by means of SUSAN[125] using a Gaussian kernel of FWHM of 7 mm, and a temporal high pass filter of 100 s. Single session independent component analysis (ICA) was performed using Multivariate Exploratory Linear Optimized Decomposition into Independent Components (MELODIC ICA[126]) in order to perform automated denoising (see below). FMRIB's Linear and non-linear Image Registration Tools (FLIRT[124]) optimized using Boundary Based Registration (BBR[127]) was used to align each participant's fMRI data to a standard space (MNI-152) with the T1-weighted volume as an intermediate.

Individual level general linear models (GLM) were fitted using FILM (FMRIB's Improved Linear Model)[127-128] modeling the facial stimuli (happy/angry/ambiguous faces) and geometrical shape as events with the interspersed fixation trials as implicit baselines. Q1 and Q2 were modeled as one regressor across the different facial stimuli and shapes. Next, the average amygdala contrast-parameter estimates (COPE) were extracted from left and right amygdala masks based on the Harvard-Oxford anatomical atlas provided with FSL and submitted the values to higher-level linear mixed models in SPSS to test for main effects of condition and treatment (see below).

Pupilometry data was pre-processed using a custom made MATLAB-script. Raw data were converted into diameters, with physiologically unlikely pupil sizes (<2 mm or >9 mm) excluded from the data to remove noise (e.g., eye blinks). Each time series was split into trials with the average pupil diameter from each stimuli condition calculated. Finally, the first 8 seconds across all 20 trials for each condition were averaged to generate mean overall pupil diameters.

Statistical analysis was conducted using IBM SPSS Statistics version 22 (IBM, Armonk, N.Y) to examine the impact of treatment on amygdala activity. As described above, a linear mixed-model (LMM) approach was adopted for the analysis of amygdala activity. All models were fitted using an unstructured matrix. Experimental treatment was both a fixed and repeated effect in the LMM testing the impact of treatment on amygdala activity. The same LMM approach was used to examine differences in mean pupil diameter, COPE values for contrasts of both left and right amygdala activity between angry faces and shapes, happy faces and shapes, and happy faces and angry faces. Standardized residuals after model fitting were examined for outliers. Z-scores above 2.58 or below −2.58 were removed from the analysis. Outliers beyond these thresholds were removed from the amygdala activation datasets (1 value from the right amygdala data during the presentation of angry, happy and, ambiguous, and shape stimuli, respectively; 1 value from left amygdala anger and happy data, respectively; and 2 values from the left amygdala ambiguous and shape data, respectively). For any significant main effects (p<0.05), post-hoc tests were performed to compare each treatment condition with the adjustment of critical p values to correct for multiple comparisons using a 5% false discovery rate (FDR)[59]. The relationships between amygdala activation and; mean pupil dilation, behavioral ratings, and nasal physiology were also assessed. Finally, Bayes Factors using the Jeffreys-Zeliner-Siow prior[60] were calculated to examine the strength of evidence for both the null and alternative hypotheses.

Figure 13A:
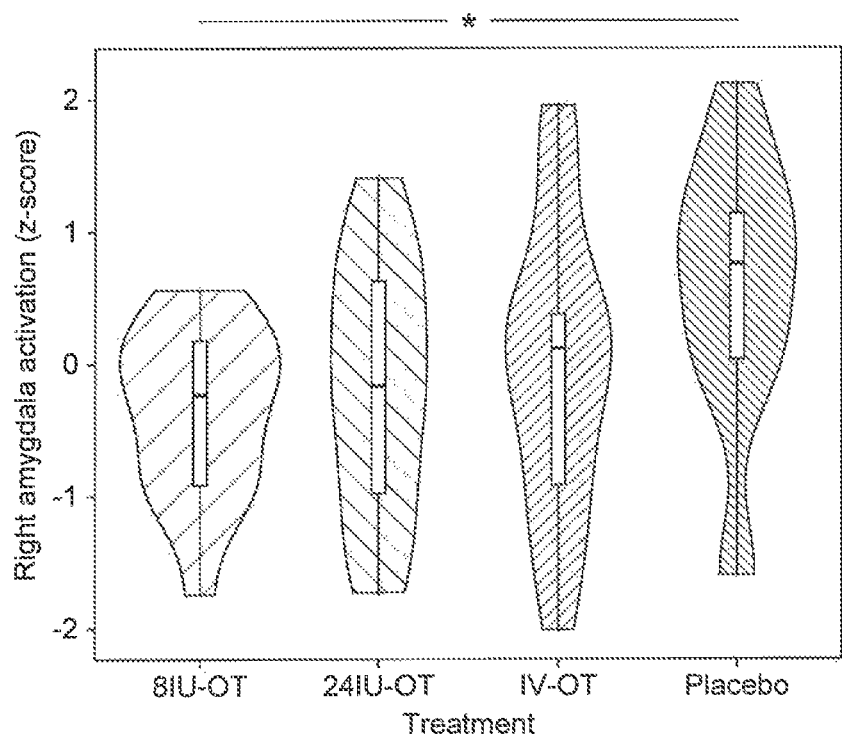
FIG. 13(a) illustrates violin plots which represent right amygdala activation and box and whisker plots which represent the median and 50% interquartile ranges after the administrations of 8 IU-OT, 24 IU-OT, IV-OT and Placebo.
Figure 13B:
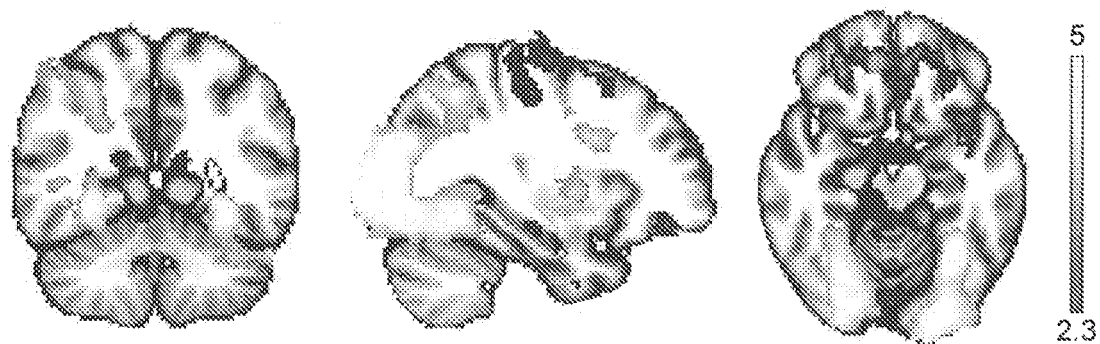
FIG. 13(b) illustrates the main effect of the presentation of faces across emotions and 8 IU-OT, 24 IU-OT, IV-OT and Placebo treatments.

LMM revealed a significant main effect of treatment on right amygdala activity during the presentation of angry faces [F(3,15.1)=4.54, p=0.019; FIGS. 13(a) and (b)]. Follow-up pairwise comparisons (q=0.05, revised critical value of p<0.008) indicated that right amygdala activation was significantly reduced in the 8 IU-OT treatment condition in comparison to placebo (p=0.002). There was a main effect of treatment on right amygdala activity in response to the presentation of happy faces [F(3,15)=3.44, p=0.04], with posthoc comparisons indicating the reduction after 8 IU-OT compared to placebo was on the border of the FDR significance threshold (p=0.01; q=0.05, revised critical value of p<0.008). There was a main effect of treatment, on the border of significance, for right amygdala activity during the presentation of ambiguous faces [F(3,14.6)=3.15, p=0.057].

Exploratory posthoc analyses revealed the reduction of right amygdala activity in the 8 IU-OT condition compared to the placebo condition was on the border of the FDR corrected significance threshold (p=0.01; q=0.05, revised critical value of p<0.008). There was also a main effect of treatment and geometric shapes [F(3,15)=3.56, p=0.04], however, post hoc analyses revealed no significant differences after FDR corrected thresholds. There was a main effect for the happy faces > angry faces contrast for the right amygdala [F(3, 14.7)=4.46, p=0.02] but no posthoc comparisons survived FDR corrected thresholds. With regard to left amygdala activity, a LMM revealed no main effect of condition during the presentation of angry faces [F(3,15.1)=1.28, p=0.32], ambiguous faces [F(3,13.6)=1.14, p=0.37], happy faces [F(3,14)=2.14, p=0.14], or geometric shapes [F(3,14.4)=1.87, p=0.18]. There was a main effect for the happy faces > angry faces contrast on left amygdala activity [F(3,14.7)=4.79, p=0.02], but no posthoc comparisons survived FDR corrected thresholds. There were no main effects of treatment for any of the emotion > shape COPE value contrasts, as represented in Table 7.

TABLE 7

COPE values for amygdala activity

|  | BIU-OT | 24IU-OT | IV-OT | Placebo | df | F | p |
|---|---|---|---|---|---|---|---|
| Right amygdala | | | | | | | |
| Angry faces > shapes | .36 (.5) | −.13 (.01) | −.12 (.01) | −.12 (.01) | 3, 15 | 0.43 | 0.74 |
| Happy faces > shapes | −.61 (.17) | .02 (.27) | −.24 (.22) | .26 (.32) | 3, 14.7 | 0.45 | 0.72 |
| Ambiguous faces > shapes | −.09 (.19) | −.22 (.33) | .16 (.23) | .14 (.24) | 3, 15.1 | 0.48 | 0.7 |
| Left amygdala | | | | | | | |
| Angry faces > shapes | −.19 (.004) | .54 (.49) | −.17 (.01) | −.18 (.01) | 3, 15 | 2.09 | 0.14 |
| Happy faces > shapes | .05 (.19) | 1.3 (.23) | −.34 (.2) | .11 (.36) | 3, 14.3 | 2.44 | 0.11 |
| Ambiguous faces > shapes | −.11 (.19) | .02 (.37) | .02 (.24) | .02 (.22) | 3, 14.8 | 0.11 | 0.95 |

Note.
Values represent z-score estimated marginal means with standard errors in parenthesis.

Figure 14C:
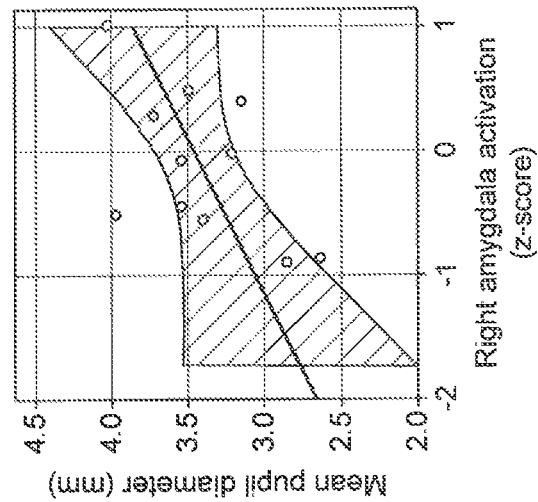
FIGS. 14(a) to (c) represent the relationship between mean pupil diameter and right amygdala activity after the 8 IU-OT treatment while processing angry, ambiguous and happy facial stimuli.
Figure 14B:
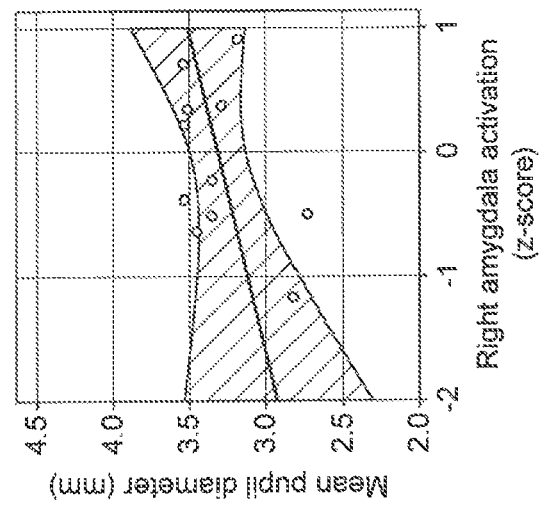
Figure 14A:
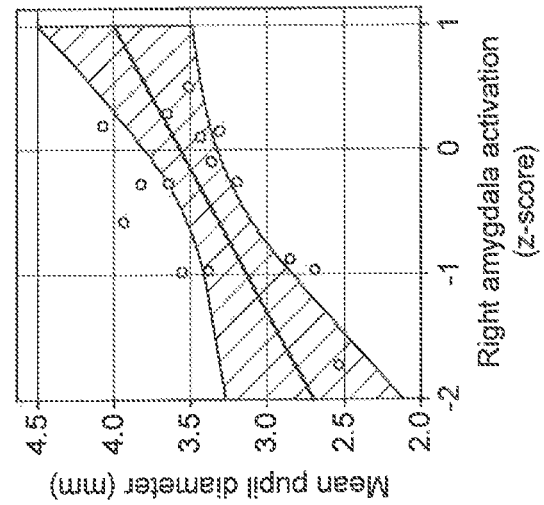

There was no significant main effect of treatment on mean pupil diameter while processing angry [F(3,15)=0.57, p=0.64], happy [F(3,15)=0.62, p=0.62], or emotionally ambiguous faces [F(3,15)=1.33, p=0.3]. However, there was a significant relationship between right amygdala activation and mean pupil diameter during the presentation of, angry (p=0.02; FIG. 14(a)), ambiguous (p<0.001; FIG. 14(b)), and happy (p=0.01; FIG. 14(c)) faces after 8 IU-OT treatment, as represented in Table 8. All the corresponding Bayes factors (B) were greater than 3, providing substantial evidence[130] that these two variables are related. There were no significant relationships after the other treatments (All p's>0.05), and all B's were less than 0.33, providing substantial evidence that none of these variables were related. Finally, there were no significant relationships between intensity of anger ratings and right amygdala activity after any of the treatments, as represented in Table 9, or between nasal valve dimensions and right amygdala activation in after any of the treatments, as represented in Table 10. As described hereinabove, there was no difference in nasal valve dimensions before each treatment administration [F(9, 108)=0.41, p=0.93]. The frequency of adverse events (e.g., brief dizziness) reported was equivalent between treatment groups (8 IU-OT, three reports; 24 IU-OT, two reports, IV OT, three reports, placebo, two reports).

TABLE 8

Relationship between pupil diameter and amygdala activation after each treatment

| | BIU-OT[a] | | | | 24IU-OT[b] | | | | IV-OT[b] | | | | Placebo[b] | | | |
|---|---|---|---|---|---|---|---|---|---|---|---|---|---|---|---|---|
| | r | (95 % CI) | p | B | r | (95 % CI) | p | B | r | (95 % CI) | p | B | r | (95 % CI) | p | B |
| Pupil diameter-Angry faces | .61 | (.14, .86) | .02 | 3.53 | .09 | (−.42, .56) | 0.73 | .2 | −.22 | (−.65, .31) | 0.4 | .26 | .24 | (−.29, .66) | .38 | .28 |
| Pupil diameter-Ambiguous faces | .79 | (.46, .93) | <.001 | 82.7 | −.04 | (−.53, .46) | 0.89 | .19 | −.11 | (−.57, .41) | .68 | .21 | .07 | (−.44, .55) | .81 | .2 |
| Pupil diameter-Happy faces | .63 | (.17, .86) | .01 | 4.53 | .02 | (−.48, .51) | 0.95 | .19 | −.18 | (−.62, .35) | .5 | .24 | .22 | (−.31, .65) | .42 | .26 |

Note.
[a]N = 15, [b]N = 16; B = Bayes Factor

TABLE 9

Relationship between anger ratings and right amygdala activation after each treatment

| | BIU-OT | | | | 24IU-OT[c] | | | | IV-OT | | | | Placebo[c] | | | |
|---|---|---|---|---|---|---|---|---|---|---|---|---|---|---|---|---|
| | r | (95 % CI) | p | B | r | (95 % CI) | p | B | r | (95 % CI) | p | B | r | (95 % CI) | p | B |
| Angry faces | .07 | (−.48, .58)[a] | .8 | .21 | .05 | (−.46, .53) | 0.87 | .19 | −.01 | (−.52, .5)[b] | .97 | .19 | .29 | (−.24, .67) | .28 | .34 |
| Happy faces | −.14 | (−.4, .61)[b] | .62 | .22 | −.42 | (−.75, .1) | 0.11 | .7 | −.47 | (−.79, .06)[b] | .07 | .93 | .21 | (−.32, .64) | .44 | .26 |
| Ambiguous faces | .03 | (−.55, .51)[a] | .92 | .2 | −.44 | (−.77, .07) | 0.09 | .81 | −.19 | (−.63, .34)[c] | .51 | .24 | −.09 | (−.56, .42) | .74 | .2 |

Note.
[a]N = 14, [b]N = 15, [c]N = 16; B = Bayes Factor.

TABLE 10

Relationship between nasal valve dimensions and right amygdala activation after each treatment

| | BIU-OT[a] | | | | 24IU-OT[b] | | | | IV-OT[b] | | | | Placebo[b] | | | |
|---|---|---|---|---|---|---|---|---|---|---|---|---|---|---|---|---|
| | r | (95 % CI) | p | B | r | (95 % CI) | p | B | r | (95 % CI) | p | B | r | (95 % CI) | p | B |
| Angry faces | −.03 | (−.53, .49) | .92 | .2 | −.07 | (−.55, .44) | .81 | .2 | .21 | (−.32, .64) | .44 | .27 | −.11 | (−.57, .41) | .68 | .21 |
| Happy faces | .03 | (−.49, .53) | .91 | .2 | −.11 | (−.57, .41) | .69 | .21 | .17 | (−.36, .61) | .54 | .23 | −.17 | (−.61, .36) | .54 | .23 |
| Ambiguous faces | −.15 | (−.62, .39) | .62 | .22 | −.03 | (−.52, .47) | .91 | .19 | −.12 | (−.58, .4) | .65 | .21 | −.17 | (−.61, .36) | .54 | .23 |

Note.
[a]N = 15, [b]N = 16; B = Bayes Factor.

In this study, 8 IU-OT treatment is shown to reduce amygdala activity in comparison to placebo. These findings are the first to report direct comparison of nose-to-brain and systemic delivery of OT, and indicate that OT delivery via nose-to-brain pathways—but not peripherally delivered OT producing similar blood levels—replicates a well-characterized finding of reduced right amygdala activation in response to emotional stimuli after OT treatment[88,114-115].

Significantly, this data is consistent with the findings as discussed above that OT delivered by the inventive device modulates the perception of anger in facial stimuli and with animal models that associated a lower OT dose with stronger increases in social recognition[69-70], which is pertinent given the important role of the amygdala in social cognition and behavior.

These effects may not be specific to negatively-valenced social stimuli as the main effects of treatment on right amygdala activity during the presentation of happy and ambiguous faces were significant and on the border of significance, respectively. Subsequent posthoc comparisons between the 8 IU-OT treatment and placebo were on the border of statistical significance. The observed reductions in right amygdala activity during the presentation of both positively and negatively valenced stimuli after OT treatment are consistent with the hypothesis that OT increases approach-related behaviours[114,118].

Secondary analysis revealed a significant association between right amygdala activity and mean pupil diameter during the processing of angry, ambiguous, and happy facial stimuli after 8 IU-OT administration. While a main effect of treatment on pupil diameter not was found, the data is indicative of the amygdala modulating cognitive resources to facial stimuli, regardless of valence, after 8 IU-OT treatment.

The amygdala is a site of large number of oxytocin receptors[132]. These receptors have been shown to operate by inhibiting amygdala activity via the increase of GABAergic interneuron activity[133-134]. The observed decrease in amygdala activity after OT administration using the inventive device is consistent with nose-to-brain molecule transport via olfactory and trigeminal nerve fiber pathways[135]. Outputs to the amygdala via the olfactory bulbs[136-138] or transport through brain extracellular fluid[139] from olfactory bulb and brainstem delivery sites may facilitate these reductions in amygdala activity via a local GABAergic circuit after intranasal delivery. Irrespective of how endogenous OT precisely affects amygdala activity, by having a peripheral comparator this study demonstrates that nose-to-brain pathways produce effects not observed with comparable levels of purely systemic exposure, suggesting facilitated entry to the brain.

The dose-response data reported here suggest that a low dose of OT delivered using the inventive device is sufficient to modulate amygdala activity. Patients with underlying deficits responsive to OT may respond more robustly than healthy volunteers.

There are a number of reasons that may explain why an effect was found with the 8 IU-OT dose but not the 24 IU-OT. These include cross reactivity with vasopressin receptors[49] and the possibility that an 8 IU-OT dose delivered with the inventive device is better able to reach the regions in the nose where direct nose-to-brain transport can occur.

Significantly, no evidence was found that 1 IU-OT of peripherally administered OT influences amygdala activity. Although there is conflicting evidence on whether peripheral OT can cross the BBB[140-141], our study suggests that even if OT does travel across this barrier in small amounts, this quantity is not large enough to modulate amygdala activity compared to placebo. Individual differences and context can influence the response to OT administration[16], thus a strength of this study was the use of a within-subjects design to examine amygdala activity. By adopting this experimental design, any individual differences due to variation in the endogenous oxytocin system[141-143] are minimized.

In summary, the present study shows surprisingly that a low dose of OT intranasally delivered with the described delivery method modulates amygdala activity, and this result provides additional evidence to suggest a lower intranasal OT dose may better facilitate the modulation of social cognition and behavior and that peripheral actions of OT do not appear to have any significant neural corollaries.

REFERENCES

1. Guastella A J, MacLeod C (2012): A critical review of the influence of oxytocin nasal spray on social cognition in humans: Evidence and future directions. *Horm Behav.* 61:410-418.
2. Meyer-Lindenberg A, Domes G, Kirsch P, Heinrichs M. Oxytocin and vasopressin in the human brain: social neuropeptides for translational medicine. Nat Rev Neurosci 2011; 12: 524-538.
3. Striepens N, Kendrick K M, Maler W, Huriemann R. Prosocial effects of oxytocin and clinical evidence for its therapeutic potential. Front Neuroendocrinol 2011; 32:426-450.
4. Bartz J A, Zaki J, Bolger N, Hollander E, Ludwig N N, Kolevzon A, et al (2010): Oxytocin Selectively Improves Empathic Accuracy. *Psychol Sci.* 21:1426-1428.
5. Hurlemann R, Patin A, Onur O A, Cohen M X, Baumgartner T, Metzler S et al. Oxytocin enhances amygdala-dependent, socially reinforced learning and emotional empathy in humans. J Neurosci 2010; 30: 4999-5007.
6. Kosfeld M, Heinrichs M, Zak P J, Fischbacher U, Fehr E. Oxytocin increases trust in humans. Nature 2005; 435: 673-676.
7. Shalvi S, De Dreu C K. Oxytocin promotes group-serving dishonesty. Proc Nati Acad Sci USA 2014; 111: 5503-5507.
8. Van Ijzendoorn M H, Bakermans-Kranenburg M J. A sniff of trust: meta-analysis of the effects of intranasal oxytocin administration on face recognition, trust to ingroup, and trust to out-group. Psychoneuroendocrinology 2012; 37: 438-443.
9. Guastella A J, Mitchell P B, Dadds M R (2008): Oxytocdn Increases gaze to the eye region of human faces. *Biol Psychiatry.* 63:3-5.
10. Domes G, Heinrichs M, Michel A, Berger C, Herpertz S C (2007): Oxytocin Improves "Mind-Reading" in Humans. *Biol Psychiatry.* 61:731-733.
11. Guastella A J, Einfeld S L, Gray K M, Rinehart N J, Tonge B J, Lambert T J, et al (2010): Intranasal Oxytocin Improves Emotion Recognition for Youth with Autism Spectrum Disorders. *Biol Psychiatry.* 67:692-694.
12. Modi M E, Young U (2012): The oxytocin system in drug discovery for autism: Animal models and novel therapeutic strategies. *Horm Behav.* 61:340-350.
13. MacDonald K, Feifel D (2012): Oxytocin in schizophrenia: a review of evidence for its therapeutic effects. *Acta Neuropsychiatrica.* 24:130-146.
14. Dadds M R, MacDonald E, Cauchi A, Williams K, Levy F, Brennan J (2014): Nasal oxytocin for social deficits in childhood autism: A randomized controlled trial. *J Autism Dev Disord.* 44:521-531.
15. Guastella A J, Hickie I B, McGuinness M M, Otis M, Woods E A, Disinger H M, et al (2013): Recommendations for the standardisation of oxytocin nasal administration and guidelines for its reporting in human research. *Psychoneuroendocrinology.* 38:612-625.
16. Bartz J A, Zaki J, Boiger N, Ochsner K N (2011): Social effects of oxytocin in humans: context and person matter. *Trends in cognitive sciences.* 15:301-309.
17. MacDonald K, Feifel D (2013): Helping oxytocin deliver: considerations in the development of oxytocin-based therapeutics for brain disorders. *Front Neurosci.*
18. Quintana D S, Alvares G A, Hickle I B, Guastella A J (2015): Do delivery routes of intranasally administered oxytocin account for observed effects on social cognition and behavior? A two-level model. *Neurosci Biobehav Rev.* 49:182-192.
19. Landgraf R, Neumann I D. Vasopressin and oxytocin release within the brain: a dynamic concept of multiple and variable modes of neuropeptide communication. Front Neuroendocrinol 2004; 25: 150-176.
20. Iliff J J, Wang M, Liao Y, Plogg B A, Peng W, Gundersen G A et al. A paravascular pathway facilitates CSF flow through the brain parenchyma and the clearance of interstitial solutes, including amyloid $\beta$. Sci Trans) Med 2012; 4:147ra111-147ra111.
21. Dhuria S V, Hanson L R, Frey W H II. Intranasal delivery to the central nervous system: Mechanisms and experimental considerations. J Pharm Sci 2009; 99:1654-1673.
22. Ermisch A, Barth T, Ruhle H, Skopkova 3, Hrbas P, Landgraf R. On the blood-brain barrier to peptides: accumulation of labelled vasopressin, DesGlyNH2-vasopressin and oxytocin by brain regions. Endocrinol Exp 1985; 19: 29-37.
23. Djupesland P G, Messina J C, Mahmoud R A (2014): The nasal approach to delivering treatment for brain diseases: an anatomic, physiologic, and delivery technology overview. *Therapeutic delivery.* 5:709-733.
24. Cole P (2003): The four components of the nasal valve. *Am J Rhinol.* 17:107-110.
25. Aggarwal R, Cardozo A, Homer J. The assessment of topical nasal drug distribution. Clin Otolaryngol Allied Sci 2004; 29: 201-205.
26. Djupesland P G, Skretting A, Winderen M, Holand T (2006): Breath Actuated Device Improves Delivery to Target Sites Beyond the Nasal Valve. *The Laryngoscope.* 116:466-472.
27. Djupesland P G, Messina J C, Mahmoud R A. Breath powered nasal delivery: a new route to rapid headache relief. Headache 2013; 53: 72-84.
28. Eccles R. Nasal airflow in health and disease. Acta Otolaryngol 2000; 120: 580-595.
29. Merkus P, Ebbens F A, Muller B, Fokkens W J. Influence of anatomy and head position on intranasal drug deposition. Eur Arch Otorhinolaryngol 2006; 263:827-832.
30. Djupesland P G, Mahmoud R A, Messina J C (2013): Accessing the brain: the nose may know the way. *Journal of Cerebral Blood Flow & Metabolism.* 33:793-794.
31. Djupesland P G, Skretting A (2012): Nasal Deposition and Clearance in Man: Comparison of a Bidirectional Powder Device and a Traditional Liquid Spray Pump. *Journal of Aerosol Medicine and Pulmonary Drug Delivery.* 25:280-289.
32. Djupesland P G (2012): Nasal drug delivery devices: characteristics and performance in a clinical perspective—a review. *Drug Delivery and Translational Research* 2012; 3:42-62.
33. Hollander E, Novotny S, Hanratty M, Yaffe R, DeCaria C M, Aronowitz B R, et al (2003): Oxytocin Infusion Reduces Repetitive Behaviors in Adults with Autistic and Asperger' s Disorders. *Neuropsychopharmacology.* 28:193-198.
34. Hollander E, Bartz J, Chaplin W, Phillips A, Sumner J, Soorya L, et al (2007): Oxytocin Increases Retention of Social Cognition in Autism. *Biol Psychiatry.* 61:498-503.

35. Striepens N, Kendrick K M, Hanking V, Landgraf R, Wüliner U, Maler W et al. Elevated cerebrospinal fluid and blood concentrations of oxytocin following its intranasal administration in humans. Sci Rep 2013; 3: 3440.
36. MacDonald E, Dadds M R, Brennan J L, Williams K, Levy F, Cauchi A J (2011): A review of safety, side-effects and subjective reactions to intranasal oxytocin in human research. *Psychoneuroendocrinology.* 36:1114-1126.
37. Bakermans-Kranenburg M, Van Ijzendoorn M (2013): Sniffing around oxytocin: review and meta-analyses of trials in healthy and clinical groups with implications for pharmacotherapy. *Translational psychiatry.* 3:e258.
38. de Oliveira D C, Zuardi A W, Graeff F G, Queiroz R H, Crippa J A (2012): Anxiolytic-like effect of oxytocin in the simulated public speaking test. *J Psychopharmacol (Oxf).* 26:497-504.
39. Butwick A, Coleman L, Cohen S, Riley E, Carvalho B (2010): Minimum effective bolus dose of oxytocin during elective Caesarean delivery. *Br J Anaesth.* 104:338-343.
40. Rault J-L, Carter C S, Gamer J P, Marchant-Forde J N, Richert B T, Lay Jr D C (2013): Repeated intranasal oxytocin administration in early life dysregulates the HPA axis and alters social behavior. *Physiol Behav.* 112:40-48.
41. Gimpl G, Fahrenholz F (2001): The oxytocin receptor system: structure, function, and regulation. *Physiol Rev.* 81:629-683.
42. Mayer-Hubner B (1996): Pseudotumour cerebri from intranasal oxytocin and excessive fluid intake. *The Lancet.* 347:623-623.
43. Kanat M, Heinrichs M, Schwarzwald R, Domes G. Oxytocin attenuates neural reactivity to masked threat cues from the eyes. Neuropsychopharmacology 2015; 40: 287-295.
44. Evans S, Shergill S S, Averbeck B B. Oxytocin decreases aversion to angry faces in an associative learning task. Neuropsychopharmacology 2010; 35: 2502-2509.
45. Domes G, Steiner A, Porges S W, Heinrichs M. Oxytocin differentially modulates eye gaze to naturalistic social signals of happiness and anger. Psychoneuroendocrinology 2013; 38: 1198-1202.
46. Jesso S, Morlog D, Ross S, Pell M D, Pasternak S H, Mitchell D G et al. The effects of oxytocin on social cognition and behaviour in frontotemporal dementia. Brain 2011; 134: 2493-2501.
47. Bertsch K, Gamer M, Schmidt B, Schmidinger I, Walther S, Kastel T et al. Oxytocin and reduction of social threat hypersensitivity in women with borderline personality disorder. Am J Psychiatry 2013; 170: 1169-1177.
48. MacDonald K, Feifel D. Oxytocin's role in anxiety: a critical appraisal, Brain Res 2014; 1580: 22-56.
49. Neumann I D, Landgraf R (2012): Balance of brain oxytocin and vasopressin: implications for anxiety, depression, and social behaviors. *Trends Neurosci.* 35:649-659.
50. Legros J, Chiodera P, Geenen V, Smitz S, Frenckell Rv (1984): Dose-Response Relationship between Plasma Oxytocin and Cortisol and Adrenocorticotropin Concentrations during Oxytocin Infusion in Normal Men*. *The Journal of Clinical Endocrinology & Metabolism.* 58:105-109.
51. Neumann I D. Involvement of the brain oxytocin system in stress coping: Interactions with the hypothalamo-pituitary-adrenal axis. Prog Brain Res 2002; 139: 147-162.
52. Wechsler D (1999): *Weschsler Abbreviated Scale of Intelligence.* San Antonio, Tex.: Psychological Corporation.
53. Lecrubier Y, Sheehan D, Weiller E, Amorim P, Bonora I, Harnett Sheehan K, et al (1997): The Mini International Neuropsychiatric Interview (MINI). A short diagnostic structured interview: reliability and validity according to the CIDI. *Eur Psychiatry.* 12:224-231.
54. Spielberger C D (1983): Manual for the State-Trait Anxiety Inventory STAI (form Y)("self-evaluation questionnaire").
55. Leknes S, Wessberg J, Ellingsen D M, Chelnokova O, Olausson H, Laeng B (2012): Oxytocin enhances pupil dilation and sensitivity to 'hidden' emotional expressions. *Soc Cogn Affect Neurosci.* 8:741-749.
56. Lundqvist D, Flykt A, Öhman A (1998): The Karolinska directed emotional faces (KDEF). *C D ROM from Department of Clinical Neuroscience, Psychology section, Karolinska Institutet.* 91-630.
57. McCullough M E, Churchiand P S, Mendez A J. Problems with measuring peripheral oxytocin: can the data on oxytocin and human behavior be trusted? NeurosciBiobehav Rev 2013; 37: 1485-1492.
58. Hamer R, Simpson P (2009): Last observation carried forward versus mixed models in the analysis of psychiatric clinical trials. *Am J Psychiatry.* 166:639-641.
59. Benjamini Y, Hochberg Y (1995): Controlling the false discovery rate: a practical and powerful approach to multiple testing. *Journal of the Royal Statistical Society Series B (Methodological).* 289-300.
60. Wetzels R, Wagenmakers, E-J (2012). A default Bayesian hypothesis test for correlations and partial correlations. Psychon. Bull. Rev. 19, 1057-1064.
61. Zou G Y (2007). Toward using confidence intervals to compare correlations. Psychol. Methods 12, 399.
62. Raghunathan T, Rosenthal R, Rubin, D B (1996). Comparing correlated but nonoverlapping correlations. Psychol. Methods 1, 178.
63. Dienes Z (2014). Using Bayes to get the most out of non-significant results. Front Psychol 2014; 5:1-17.
64. Theodoridou A, Rowe A C, Penton-Voak I S, Rogers P J (2009): Oxytocin and social perception: oxytocin increases perceived facial trustworthiness and attractiveness. *Horm Behav.* 56:128-132.
65. Van Ijzendoorn M H, Bhandari R, Van der Veen R, Grewen K M, Bakermans-Kranenburg M J (2012): Elevated salivary levels of oxytocin persist more than 7 h after intranasal administration. *Front Neurosci.* 6.
66. Cardoso C, Ellenbogen M A, Orlando M A, Bacon S L, Joober R (2013): Intranasal oxytocin attenuates the cortisol response to physical stress: a dose-response study. *Psychoneuroendocrinology.* 38:399-407.
67. Hall S S, Lightbody A A, McCarthy B E, Parker K J, Reiss A L (2012): Effects of intranasal oxytocin on social anxiety in males with fragile X syndrome. *Psychoneuroendocrinology.* 37:509-518.
68. Bales K L, Perkeybile A M, Conley O G, Lee M H, Guoynes C D, Downing G M, et al (2013): Chronic intranasal oxytocin causes long-term impairments in partner preference formation in male prairie voles. *Biol Psychiatry.* 74:180-188.
69. Benelli A, Bertolini A, Poggloll R, Menozzi B, Basaglia R, Arletti R (1995): Polymodal dose-response curve for oxytocin in the social recognition test. *Neuropeptides.* 28:251-255.
70. Poplk P, Vetulani J, Van Ree J M (1992): Low doses of oxytocin facilitate social recognition in rats. *Psychopharmacology (Berl).* 106:71-74.
71. Bloom D E, Cafiero E, Jand-Llopis E, Abrahams-Gessel S, Bloom L R, Fathima S et al. The Global Economic Burden of Noncommunicable Diseases: Program on the Global Demography of Aging, 2012.
72. Miller G. Is pharma running out of brainy ideas. Science 2010; 329: 502-504.
73. Abbott A. Novartis to shut brain research facility. Nature 2011; 480: 161-162.
74. Frank E, Landgraf R (2008): The vasopressin system—from antidiuresis to psychopathology. *Eur J Pharmacol.* 583:226-242.
75. U C, Wang W, Summer S N, Westfall T D, Brooks D P, Falk S, et al (2008): Molecular mechanisms of antidiuretic effect of oxytocin. *J Am Soc Nephrol.* 19:225-232.
76. Weisman O, Schneiderman I, Zagoory-Sharon O, Feldman R. Salivary vasopressin increases following intranasal oxytocin administration. Peptides 2013; 40: 99-103.
77. Burri A, Heinrichs M, Schedlowski M, Kruger T H. The acute effects of intranasal oxytocin administration on endocrine and sexual function in males. Psychoneuroendocrlnology 2008; 33: 591-600.
78. Gossen A, Hahn A, Westphal L, Prinz S, Schultz R, Gründer G et al. Oxytocin plasma concentrations after single intranasal oxytocin administration-A study in healthy men. Neuropeptides 2012; 46: 211-215.
79. Charlton S, Davis S, IlIum L. Nasal administration of an angiotensin antagonist in the rat model: effect of bloadhesive formulations on the distribution of drugs to the systemic and central nervous systems. Int J Pharm 2007; 338: 94-103.
80. Dale O, Nilsen T, Loftsson T, Tennesen H H, Klepstad P, Kaasa S et al. Intranasal midazolam: a comparison of two delivery devices in human volunteers. J Pharm Pharmacol 2006; 58: 1311-1318.
81. Shahrestani S, Kemp A H, Guastella A J (2013): The impact of a single administration of intranasal oxytocin on the recognition of basic emotions in humans: a meta-analysis. *Neuropsychopharmacology.* 38:1929-1936.
82. Guastella A J, Howard A L, Dadds M R, Mitchell P, Carson D S (2009): A randomized controlled trial of intranasal oxytocin as an adjunct to exposure therapy for social anxiety disorder. *Psychoneuroendocrlnology.* 34:917-923.
83. Elford R C, Nathan P J, Auyeung B, Mogg K, Bradley B P, Sule A et al.
Effects of oxytocin on attention to emotional faces in healthy volunteers and highly socially anxious males. Int J Neuropsychopharmacol 2014; 18: 1-11.
84. Alvares G A, Chen N T M, Balleine B W, Hickie I B, Guastella A J (2012): Oxytocin selectively moderates negative cognitive appraisals in high trait anxious males. *Psychoneuroendocrinology.* 37:2022-2031.
85. Fisher R A (1935). The design of experiments.
86. LeDoux J E (2001). Emotion circuits in the brain. The Science of Mental Health: Fear and anxiety 259.
87. Seeley W W, Menon V, Schatzberg A F, Keller J, Glover G H, Kenna H, Reiss A L, Greicius M D (2007). Dissociable intrinsic connectivity networks for salience processing and executive control. The Journal of neuroscience 27, 2349-2356.
88. Domes G, Heinrichs M, Gläscher J, Buchel C, Braus D F, Herpertz S C (2007). Oxytocin attenuates amygdala responses to emotional faces regardless of valence. Biol. Psychiatry 62, 1187-1190.
89. Kirsch P, Esslinger C, Chen Q, Mier D, Lis S, Siddhanti S, Gruppe H, Mattay V S, Galihofer B, Meyer-Lindenberg A (2005). Oxytocin modulates neural circuitry for social cognition and fear in humans. The Journal of neuroscience 25, 11489-11493.
90. Domes G, Lischke A, Berger C, Grossmann A, Hauenstein K, Heinrichs M, Herpertz S C (2010). Effects of intranasal oxytocin on emotional face processing in women. Psychoneuroendocrinology 35, 83-93.
91. Gamer M, Zurowski B, Buchel C (2010). Different amygdala subregions mediate valence-related and attentional effects of oxytocin in humans. PNAS 107, 9400-9405.
92. Paloyelis Y, Doyle O M, Zelaya F O, Maltezos S, Williams S C, Fotopoulou A, Howard M A (2014). A Spatiotemporal Profile of in vivo Cerebral Blood Flow Changes Following Intranasal Oxytocin in Humans. Biol. Psychiatry.
93. Sripada C S, Phan K L, Labuschagne I, Welsh R, Nathan P J, Wood A G, (2013). Oxytocin enhances resting-state connectivity between amygdala and medial frontal cortex. The International Journal of Neuropsychopharmacology 16, 255-260.
94. Salvador R, Sarro S, Gomar J J, Ortiz-Gil J, Vila F, Capdevila A, Bulimore E, McKenna P J, Pomarol-Ciotet E (2010). Overall brain connectivity maps show corticosubcortical abnormalities in schizophrenia. Hum. Brain Mapp. 31, 2003-2014.
95. Lapidus K A, Levitch C F, Perez A M, Brallier J W, Parides M K, Soleimani L, et al (2014): A Randomized Controlled Trial of Intranasal Ketamine in Major Depressive Disorder. *Biol Psychiatry.*
96. Ebert A, Kolb M, Heller J, Edel M-A, Roser P, BrOne M (2013): Modulation of interpersonal trust in borderline personality disorder by intranasal oxytocin and childhood trauma. *Soc Neurosci.* 8:305-313.
97. Klacki J, Pfundmair M, Agroskin D, Jonas E (2013): Who is to blame? Oxytocin promotes nonpersonalistic attributions in response to a trust betrayal. *Biol Psychol.* 92:387-394.
98. Åkerlund M, Bossmar T, Brouard R, Kostrzewska A, Laudanski T, Lemancewicz A, et al (1999): Receptor binding of oxytocin and vasopressin antagonists and inhibitory effects on isolated myometrium from preterm and term pregnant women. *BJOG: An International Journal of Obstetrics & Gynaecology.* 106:1047-1053.
99. Manning M, Misicka A, Olma A, Bankowski K, Stoev S, Chini B, et al (2012): Oxytocin and vasopressin agonists and antagonists as research tools and potential therapeutics. *J Neuroendocrinol.* 24:609-628.
100. Parker K J, Buckmaster C L, Schatzberg A F, Lyons D M (2005): Intranasal oxytocin administration attenuates the ACTH stress response in monkeys. *Psychoneuroendocrinology.* 30:924-929.
101. Calcagnoli F, Meyer N, de Boer S F, Althaus M, Koolhaas J M (2014): Chronic enhancement of brain oxytocin levels causes enduring anti-aggressive and prosocial explorative behavioral effects in male rats. *Horm Behav.* 65:427-433.
102. McGregor I S, Bowen M T (2012): Breaking the loop: oxytocin as a potential treatment for drug addiction. *Horm Behav.* 61:331-339.
103. Quintana D S, Guastella A J, Westlye L T, Andreassen O A (in press): The promise and pitfalls of intranasally administering psychopharmacological agents for the treatment of psychiatric disorders. *Mol Psychiatry.*
104. McEwen B B (2004): Brain-fluid barriers: relevance for theoretical controversies regarding vasopressin and oxytocin memory research. *Adv Pharmacol.* 50:531-592.
105. Pardridge W M (1998): CNS drug design based on principles of blood-brain barrier transport. *J Neurochem.* 70:1781-1792.

106. Fjellestad-Paulsen A, Sdderberg-Ahim C, Lundin S (1995): Metabolism of vasopressin, oxytocin, and their analogues in the human gastrointestinal tract. *Peptides.* 16:1141-1147.
107. Leng G, Ludwig M (2015): Intranasal oxytocin: myths and delusions. *Biol Psychiatry.*
108. Quintana D S, Alvares G A, Hickie 1B, Guastella A J (2015): Do delivery routes of intranasally administered oxytocin account for observed effects on social cognition and behavior? A two-level model. *Neurosci Biobehav Rev.* 49:182-192.
109. Quintana D S, Woolley J D (2015): Intranasal oxytocin mechanisms can be better understood but its effects on social cognition and behavior are not to be sniffed at. *Biol Psychiatry.*
110. Guastella A J, Hickie I B (2015): Oxytocin treatment, circuitry and autism: a critical review of the literature placing oxytocin into the autism context. *Biol Psychiatry.*
111. Yamasue H (2015): Promising evidence and remaining issues regarding the clinical application of oxytocin in autism spectrum disorders. *Psychiatry Clin Neurosci.*
112. Quintana D S, Westlye L T, Rustan ØG, Tesli N, Poppy C L, Smevik H, et al. (2015): Low dose oxytocin delivered intranasally with Breath Powered device affects social-cognitive behavior: a randomized 4-way crossover trial with nasal cavity dimension assessment. *Translational Psychiatry.* 5:1-9.
113. Ousdal O, Jensen J, Server A, Hariri A, Nakstad P, Andreassen O (2008): The human amygdala is involved in general behavioral relevance detection: evidence from an event-related functional magnetic resonance imaging Go-NoGo task. *Neuroscience.* 156:450-455.
114. Labuschagne I, Phan K L, Wood A, Angstadt M, Chua P, Heinrichs M, et al. (2010): Oxytocin Attenuates Amygdala Reactivity to Fear in Generalized Social Anxiety Disorder. *Neuropsychopharmacology.* 35:2403-2413.
115. Petrovic P, Kalisch R, Singer T, Dolan R J (2008): Oxytocin Attenuates Affective Evaluations of Conditioned Faces and Amygdala Activity. *J Neurosci.* 28:6607-6615.
116. Riem M M, Bakermans-Kranenburg M J, Pieper S, Tops M, Boksem M A, Vermeiren R R, et al. (2011): Oxytocin modulates amygdala, insula, and inferior frontal gyrus responses to infant crying: a randomized controlled trial. *Biol Psychiatry.* 70:291-297.
117. Riem M M, van Izendoorn M H, Tops M, Boksem M A, Rombouts S A, Bakermans-Kranenburg M J (2012): No laughing matter: intranasal oxytocin administration changes functional brain connectivity during exposure to infant laughter. *Neuropsychopharmacology.* 37:1257-1266.
118. Kemp A H, Guastella A J (2011): The role of oxytocin in human affect a novel hypothesis. *Current Directions in Psychological Science.* 20:222-231.
119. Bradley M M, Miccoli L, Escrig M A, Lang P J (2008): The pupil as a measure of emotional arousal and autonomic activation. *Psychophysiology.* 45:602-607.
120. Prehn K, Heekeren H R, Van der Meer E (2011): Influence of affective significance on different levels of processing using pupil dilation in an analogical reasoning task. *Int J Psychophysiol.* 79:236-243.
121. Prehn K, Kazzer P, Lischke A, Heinrichs M, Herpertz S C, Domes G (2013): Effects of intranasal oxytocin on pupil dilation indicate increased salience of socioaffective stimuli. *Psychophysiology.* 50:528-537.
122. Djupesland P G, Mahmoud R A, Messina J C (2013): Accessing the brain: the nose may know the way. *Journal of Cerebral Blood Flow & amp; amp; Metabolism.* 33:793-794.
123. Fischi B, Salat D H, Busa E, Albert M, Dieterich M, Haselgrove C, et al. (2002): Whole brain segmentation: automated labeling of neuroanatomical structures in the human brain. *Neuron.* 33:341-355.
124. Jenkinson M, Bannister P, Brady M, Smith S (2002): Improved optimization for the robust and accurate linear registration and motion correction of brain images. *Neuroimage.* 17:825-841.
125. Smith S M, Brady J M (1997): SUSAN—A new approach to low level image processing. *International journal of computer vision.* 23:45-78.
126. Beckmann C F, Smith S M (2004): Probabilistic independent component analysis for functional magnetic resonance imaging. *Medical Imaging, IEEE Transactions on.* 23:137-152.
127. Greve D N, Fischi B (2009): Accurate and robust brain image alignment using boundary-based registration. *Neuroimage.* 48:63-72.
128. Woolrich M W, Ripley B D, Brady M, Smith S M (2001): Temporal autocorrelation in univariate linear modeling of FMRI data. *Neuroimage.* 14:1370-1386.
129. Smith S M, Jenkinson M, Woolrich M W, Beckmann C F, Behrens T E, Johansen-Berg H, et al. (2004): Advances in functional and structural M R image analysis and implementation as FSL. *Neuroimage.* 23:S208-S219.
130. Jeffreys H (1998): *The theory of probability*. Oxford, U K: Oxford University Press.
131. Veinante P, Freund-Mercier M J (1997): Distribution of oxytocin- and vasopressin-binding sites in the rat extended amygdala: a histoautoradiographic study. *J Comp Neurol.* 383:305-325.
132. Insel T R, Shapiro L E (1992): Oxytocin receptor distribution reflects social organization in monogamous and polygamous voles. *Proceedings of the National Academy of Sciences.* 89:5981-5985.
133. Huber D, Veinante P, Stoop R (2005): Vasopressin and oxytocin excite distinct neuronal populations in the central amygdala. *Science.* 308:245-248.
134. Knobloch H S, Charlet A, Hoffmann L C, Eliava M, Khrulev S, Cetin A H, et al. (2012): Evoked axonal oxytocin release in the central amygdala attenuates fear response. *Neuron.* 73:553-566.
135. Thorne R G, Pronk G J, Padmanabhan V, Frey I, W H (2004): Delivery of insulin-like growth factor-I to the rat brain and spinal cord along olfactory and trigeminal pathways following intranasal administration. *Neuroscience.* 127:481-496.
136. Ikemoto S (2007): Dopamine reward circuitry: Two projection systems from the ventral midbrain to the nucleus accumbens-olfactory tubercle complex. *Brain Research Reviews.* 56:27-78.
137. Kang N, Baum M J, Cherry J A (2011): Different Profiles of Main and Accessory Olfactory Bulb Mitral/Tufted Cell Projections Revealed in Mice Using an Anterograde Tracer and a Whole-Mount, Flattened Cortex Preparation. Chem Senses. 36:251-260.
138. Sosulski D L, Bloom M L, Cutforth T, Axel R, Datta S R (2012): Distinct representations of olfactory information in different cortical centres. *Nature.* 472:213-216.
139. Neumann I D, Maloumby R, Beiderbeck D I, Lukas M, Landgraf R (2013): Increased brain and plasma oxytocin after nasal and peripheral administration in rats and mice. *Psychoneuroendocrinology.* 38:1985-1993.

140. Mens W B, Witter A, Van Wimersma Greidanus T B (1983): Penetration of neurohypophyseal hormones from plasma into cerebrospinal fluid (CSF): half-times of disappearance of these neuropeptides from CSF. *Brain Res.* 262:143-149.
141. Modi M E, Connor-Stroud F, Landgraf R, Young L, Parr L A (2014): Aerosolized oxytocin increases cerebrospinal fluid oxytocin in rhesus macaques. *Psychoneuroendocrinology.* 45:49-57.
142. Gouin J-P, Carter C S, Poumajafi-Nazarloo H, Glaser R, Malarkey W B, Loving T J, et al. (2010): Marital behavior, oxytocin, vasopressin, and wound healing. *Psychoneuroendocrinology.* 35:1082-1090.
143. Rodrigues S M, Saslow L R, Garcia N, John O P, Keltner D (2009): Oxytocin receptor genetic variation relates to empathy and stress reactivity in humans. *Proceedings of the National Academy of Sciences.* 106: 21437-21441.

The invention claimed is:

1. A delivery device for modulating a condition in a human subject, comprising:
   a mouthpiece configured to fit within an oral cavity of the subject and permit the subject to exhale therethrough, whereby exhalation by the subject causes closure of an oropharyngeal velum of the subject;
   a nosepiece fluidly connected to the mouthpiece and configured to fit within a nostril of the subject, wherein the device is configured to deliver an exhalation breath of the subject from the mouthpiece, through the nosepiece and into a nasal cavity of the subject; and
   a delivery pump manually actuatable, on each actuation, to deliver a metered dose of a peptide through the nosepiece to an upper posterior region of the nasal cavity, posterior of a nasal valve of the subject, innervated by the trigeminal nerve, each metered dose containing less than 24 IU.

2. The delivery device of claim 1, wherein the peptide comprises Orexin-A.

3. The delivery device of claim 2, wherein the peptide is for the treatment of narcolepsy.

4. The delivery device of claim 1, wherein the peptide comprises insulin.

5. The delivery device of claim 4, wherein the peptide is for the treatment of diabetes.

6. The delivery device of claim 1, wherein the peptide is delivered as a liquid spray.

7. The delivery device of claim 1, wherein each dose contains less than 15 IU.

8. The delivery device of claim 1, wherein each dose contains greater than 1 IU.

9. The delivery device of claim 1, wherein the nasal valve is expanded by fitting of the nosepiece to have a cross-sectional area which is at least 1.5 times an unexpanded cross-sectional area of the nasal valve.

10. The delivery device of claim 1, wherein the nosepiece includes a tip which extends into and expands the nasal valve.

11. The delivery device of claim 1, wherein the nosepiece comprises a base portion defining a flow passage therethrough, and a projection at a distal end of the base portion providing a tip configured to extend into and expand the nasal valve, the projection having a rigidity in a sagittal direction and a flexibility in a lateral direction, orthogonal to a sagittal plane.

12. A method of modulating a condition in a human subject, comprising:
   fitting a mouthpiece to an oral cavity of the subject;
   fitting a nosepiece fluidly connected to the mouthpiece to a nostril of the subject;
   the subject exhaling through the mouthpiece to deliver an exhalation breath from the mouthpiece, through the nosepiece and into a nasal cavity of the subject; and
   manually actuating a delivery pump, on each actuation, to deliver a metered dose of a peptide through the nosepiece to an upper posterior region of the nasal cavity, posterior of a nasal valve of the subject, innervated by the trigeminal nerve, each metered dose containing less than 24 IU.

13. The method of claim 12, wherein the peptide comprises Orexin-A.

14. The method of claim 13, wherein the peptide is for the treatment of narcolepsy.

15. The method of claim 12, wherein the peptide comprises insulin.

16. The method of claim 15, wherein the peptide is for the treatment of diabetes.

17. The method of claim 12, wherein the peptide is delivered as a liquid spray.

18. The method of claim 12, wherein each dose contains less than 15 IU.

19. The method of claim 12, wherein each dose contains greater than 1 IU.

20. The method of claim 12, wherein the nasal valve is expanded by fitting of the nosepiece to have a cross-sectional area which is at least 1.5 times an unexpanded cross-sectional area of the nasal valve.

21. The method of claim 12, wherein the nosepiece includes a tip which extends into and expands the nasal valve.

22. The method of claim 12, wherein the nosepiece comprises a base portion defining a flow passage therethrough, and a projection at a distal end of the base portion providing a tip configured to extend into and expand the nasal valve, the projection having a rigidity in a sagittal direction and a flexibility in a lateral direction, orthogonal to a sagittal plane.

23. The method of claim 12, wherein delivery of the metered dose of the peptide provides for less than a 20% change in a plasma concentration of vasopressin in the subject.

* * * * *